(12) United States Patent
Behar-Cohen et al.

(10) Patent No.: US 9,610,294 B2
(45) Date of Patent: *Apr. 4, 2017

(54) METHODS AND COMPOSITIONS FOR THE TREATMENT OF FLUID ACCUMULATION IN AND/OR UNDER THE RETINA

(71) Applicants: UNIVERSITE PARIS DESCARTES, Paris (FR); ASSISTANCE PUBLIQUE HOPITAUX DE PARIS, Paris (FR); INSERM (Institut National de la Sante et de la Recherche Medicale), Paris (FR)

(72) Inventors: Francine Behar-Cohen, Paris (FR); Nicolette Farman, Paris (FR); Frederic Jaisser, Paris (FR)

(73) Assignees: INSERM (INSTITUT NATIONAL DE LA SANTE ET DE LA RECHERCHE MEDICALE), Paris (FR); UNIVERSITE PARIS DESCARTES, Paris (FR); ASSISTANCE PUBLIQUE HOPITAUX DE PARIS, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/588,785

(22) Filed: Jan. 2, 2015

(65) Prior Publication Data

US 2015/0216879 A1    Aug. 6, 2015

Related U.S. Application Data

(62) Division of application No. 13/696,345, filed as application No. PCT/EP2011/057497 on May 10, 2011, now Pat. No. 8,957,052.

(60) Provisional application No. 61/359,075, filed on Jun. 28, 2010, provisional application No. 61/359,575, filed on Jun. 29, 2010.

(30) Foreign Application Priority Data

May 10, 2010 (EP) ..................................... 10305493

(51) Int. Cl.
*A61K 31/573* (2006.01)
*A61K 9/00* (2006.01)

(52) U.S. Cl.
CPC .......... *A61K 31/573* (2013.01); *A61K 9/0048* (2013.01); *A61K 9/0051* (2013.01)

(58) Field of Classification Search
IPC ..................................................... A61K 31/573
See application file for complete search history.

(56) References Cited

U.S. PATENT DOCUMENTS

| | | | |
|---|---|---|---|
| 8,957,052 B2 | 2/2015 | Behar-Cohen et al. | |
| 2003/0158162 A1 | 8/2003 | Aiken | |
| 2004/0167109 A1* | 8/2004 | Bingaman | A61K 31/573 514/176 |
| 2005/0013845 A1 | 1/2005 | Warren et al. | |
| 2005/0143363 A1* | 6/2005 | De Juan | A61K 9/0048 514/179 |
| 2005/0245497 A1* | 11/2005 | Penfold | A61K 31/573 514/179 |
| 2007/0154520 A1* | 7/2007 | Ausborn | A61L 29/085 424/426 |

FOREIGN PATENT DOCUMENTS

WO    WO 2005079781    *    9/2005

OTHER PUBLICATIONS

International Search Report and Written Opinion for Application No. PCT/EP2011/057497 dated Jun. 14, 2011.
"Glaucoma," Brussels Eye Doctors, 1 page (2014).
"Eplerenone," MedlinePlus, 4 pages (2010).
"Experts Close in on Diabetic Retinopathy Cause," Weill Cornell Medical College: Press Release, 3 pages (2005).

* cited by examiner

*Primary Examiner* — Shirley V Gembeh
(74) *Attorney, Agent, or Firm* — Whitham, Curtis & Cook, P.C.

(57) ABSTRACT

The present invention provides methods and compositions for the treatment of fluid accumulation in and/or under the retina.

3 Claims, 5 Drawing Sheets

Sub retinal fluid (arrow) and dilation of choroid vessels (double arrow) after aldo injection in BN rats Vasodilatation of choroid vessels.
Rupture of junction between RPE cells (arrow)
Swollowing of photoreceptors segments
Sub retinal fluid (double arrow)

Retinal changes in 8 and 12 months-old GK rats
In diabetic rats, vasodilation of the choroids (double arrow upper right panel,) thickning) of the outer retina (lower right panel) is observed.

40±5 µV    P<0.05    57± 7 µV

Before injection            After treatment

Vehicle                     Spironolactone

METHODS AND COMPOSITIONS FOR THE TREATMENT OF FLUID ACCUMULATION IN AND/OR UNDER THE RETINA

CROSS-REFERENCE TO RELATED APPLICATIONS

The present application is filed as a divisional of U.S. patent application Ser. No. 13/696,345, which was filed Jan. 14, 2013, which was filed pursuant to 35 U.S.C. 371 as a U.S. National Phase application of International Patent Application No. PCT/EP2011/057497, which was filed May 10, 2011, claiming the benefit of priority to U.S. Provisional Application No. 61/359,075, which was filed on Jun. 28, 2010 and U.S. Provisional Application No. 61/359,575, which was filed Jun. 29, 2010. The entire text of the aforementioned applications is incorporated herein by reference in its entirety.

FIELD OF THE INVENTION

The present invention provides methods and compositions for the treatment of fluid accumulation in and/or under the retina.

BACKGROUND OF THE INVENTION

Ion channels and aquaporins are differentially expressed in retinal cells, and play important roles in ion and water movements that are crucial for adequate control of retinal hydration.

Among the isoforms of the AQP protein family identified so far, at least four AQPs are found to be expressed in the neural retina, AQP0, AQP1, AQP4 and AQP9. AQP0 is expressed in subpopulations of bipolar cells, amacrine cells and retinal ganglion cells (RGCs) (I. Iandiev, T. Pannicke, W. Härtig, J. Grosche, P. Wiedemann, A. Reichenbach and A. Bringmann, Localization of aquaporin-0 immunoreactivity in the rat retina, Neurosci. Lett. 426 (2007), pp. 81-86.). AQP1 is normally expressed in the outer retina in photoreceptors and in distinct amacrine cells (I. Iandiev, T. Pannicke, M. B. Reichel, P. Wiedemann, A. Reichenbach and A. Bringmann, Expression of aquaporin-1 immunoreactivity by photoreceptor cells in the mouse retina, Neurosci. Lett. 388 (2005), pp. 96-99.), whereas AQP4 is expressed predominantly in the perivascular and vitreal end feet of Müller cells and in astrocytes in the inner retina (M. J. Goodyear, S. G. Crewther and B. M. Junghans, A role for aquaporin-4 in fluid regulation in the inner retina, Vis. Neurosci. 26 (2009), pp. 159-165.).

It has been demonstrated that the alteration of amount and/or location of glial expression of AQP 4 mostly, but also of AQP1, in the retina leads to fluid accumulation in and/or under the retina. AQPs 1 and 4 were indeed found to be altered in a variety of animal model diseases, which include ischemia/reperfusion (I. Iandiev, T. Pannicke, B. Biedermann, P. Wiedemann, A. Reichenbach and A. Bringmann, Ischemia-reperfusion alters the immunolocalization of glial aquaporins in rat retina, Neurosci. Lett. 408 (2006), pp. 108-112.) and streptozotocin (STZ)-induced diabetes (I. Iandiev, T. Pannicke, B. Biedermann, A. Reichenbach, P. Wiedemann and A. Bringmann, Diabetes alters the localization of glial aquaporins in rat retina, Neurosci. Lett. 421 (2007), pp. 132-136.).

For example, after ischemia, retinal glial cells in the nerve fiber/ganglion cell layers strongly expressed AQP1 (I. Iandiev, T. Pannicke, B. Biedermann, P. Wiedemann, A. Reichenbach and A. Bringmann, Ischemia-reperfusion alters the immunolocalization of glial aquaporins in rat retina, Neurosci. Lett. 408 (2006), pp. 108-112.). Furthermore, the perivascular staining around the superficial vessels switched from AQP4 in control retinas to AQP1 in post-ischemic retinas (I. Iandiev, T. Pannicke, B. Biedermann, P. Wiedemann, A. Reichenbach and A. Bringmann, Ischemia-reperfusion alters the immunolocalization of glial aquaporins in rat retina, Neurosci. Lett. 408 (2006), pp. 108-112.). The data suggest that the glial cell-mediated water transport in the retina is altered after ischemia especially at the superficial vessel plexus.

With regards to diabetes, a micro array study demonstrated that AQP1 and AQP4 gene expression is up-regulated in the retinas of diabetic rats (1 Iandiev, T. Pannicke, B. Biedermann, A. Reichenbach, P. Wiedemann and A. Bringmann, Diabetes alters the localization of glial aquaporins in rat retina, Neurosci. Lett. 421 (2007), pp. 132-136.). Moreover, AQP 1 immunoreactivity was enhanced in glial cells located in the innermost retinal layers and those surrounding the superficial vessels in STZ-induced diabetic rats. Perivascular AQP4 expression was reportedly reduced in the superficial vessel plexus but unaltered in the inner nuclear layer (INL) (I. Iandiev, T. Pannicke, B. Biedermann, A. Reichenbach, P. Wiedemann and A. Bringmann, Diabetes alters the localization of glial aquaporins in rat retina, Neurosci. Lett. 421 (2007), pp. 132-136.).

Furthermore, it has been shown that endotoxin-induced uveitis (EIU) in rats alters the expression of Kir4.1 and AQP4 in the retina (Liu X Q, Kobayashi H, Jin Z B, Wada A, Nao-I N. Differential expression of Kir4.1 and aquaporin 4 in the retina from endotoxin-induced uveitis rat. Mol Vis. 2007 1; 13:309-17.).

Retinal degeneration has been associated with a mislocation of Kir4.1 and loss of AQP4 expression. (Yuan S, Zhang W, Ding J, Yao J, Jiang Q, Hu O. Increased sensitivity to retinal light damage in aquaporin-4 knockout mice. Exp Eye Res. 2009; 89(1):119-22.) Finally, it was demonstrated that Müller glial cells respond to excessive light with an alteration in the localization of Kir4.1 and aquaporin-4 proteins; (Localization of glial aquaporin-4 and Kir4.1 in the light-injured murine retina. Iandiev I, Pannicke T, Hollbom M, Wiedemann P, Reichenbach A, Grimm C, Reme C E, Bringmann A. Neurosci Lett. 2008; 434(3):317-21.).

In summary, in all the models of retinal diseases, associated with fluid homeostasis de regulation, AQP4, AQPI and Kir4.1 have been shown to be over or under expressed and mislocalized.

However, the molecular mechanisms regulating physiologic or pathologic hydro-ionic regulation in the retina remain unexplored.

SUMMARY OF THE INVENTION

The present invention provides methods and compositions for the treatment of fluid accumulation in and/or under the retina.

DETAILED DESCRIPTION OF THE INVENTION

Figure 1:
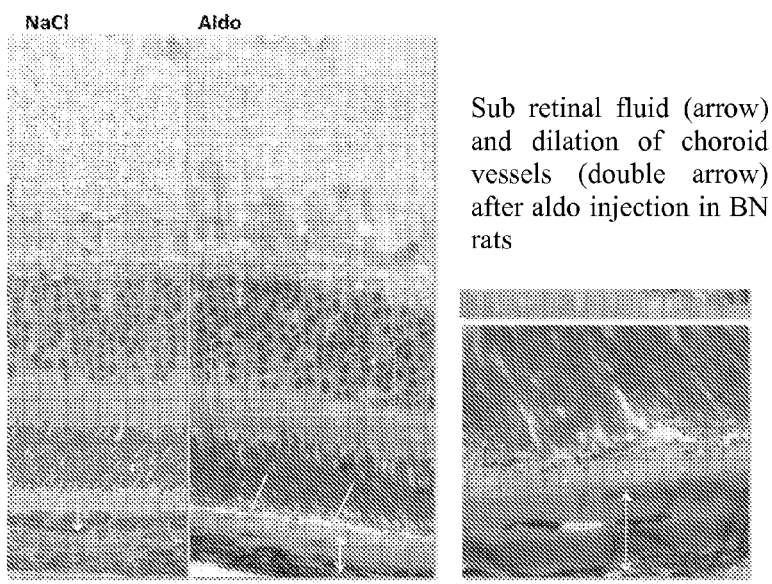
FIG. 1 depicts Brown Norway rats that carry a gain of function mutation in the MR gene, develop a retinal pathology similar to CSCR after receiving an intraocular injection of aldosterone. Sub retinal fluid (arrow) and dilation of choiroid vessels (double arrow) are indicated after aldosterone injection.

The inventors have evaluated the direct role of the MR activation on ion channels and aquaporins expression regulation on retinal Müller glial cells (RMG) in vitro, on rat organotypic culture ex vivo and on the rat retina in vivo. The results show that aldosterone regulates the expression and/or distribution of aquaporin 1, 4 and Kir4.1 in the retina.

More specifically, in the normal rat, the inventors demonstrated that already after 24 hours of exposure to low aldosterone dose (1-10 nM) enhances the expression of aquaporin 4 (AQP4) and reduces the aquaporin 1's one. More specifically, aldosterone intravitreous injection induces retinal swelling (24% increase compared to sham-injected eyes) and a strong activation of RMG. It promotes additional mislocalization of Kir4.1 and AQP4 towards apical microvilli of RMG. Therefore the results highlight the mineralocorticoid-sensitivity of the neuroretina and show that aldosterone controls hydration of the healthy retina through regulation of ion/water channels expression in RMG. Taken together, these results demonstrate that the neuroretina and more specifically RMG cells are novel targets of aldosterone and/or MR. The hormone and its receptor may therefore be considered as a novel players in the regulation of healthy retinal homeostasis and hydration.

Accordingly, the inventors now believe that upon metabolic perturbations such as diabetic retinopathy, aldosterone sensitivity of retinal tissue increase and/or aldosterone penetrates the ocular sphere due to breakdown of the hemato-retinal barriers and therefore enhances expression and mis-localization of AQP4 and Kir4.1 in RMG leading to fluid accumulation in and/or under the retina. MR antagonists may be therefore useful for the treatment of fluid accumulation in and/or under the retina as observed in metabolic perturbations such as diabetic retinopathy or in glaucoma, ischemia, myopia, central serous chorioretinitis, and the exudative forms of age related macular degeneration.

The present invention relates to a mineralocorticoid receptor (MR) antagonist for use in the treatment of fluid accumulation in and/or under the retina associated with diabetic retinopathy, glaucoma, ischemia, myopia, central serous chorioretinitis, or the exudative forms of age related macular degeneration.

As used herein, the term "mineralocorticoid receptor" or "MR" has its general meaning in the art and refers to the nuclear receptor subfamily 3, group C, member 2, (NR3C2) that is a receptor with high affinity for mineralocorticoids. The mineralocorticoid receptor is also called aldosterone receptor. The MR antagonistic or agonistic activity of a compound may be determined using various methods as described in J, Souque A, Wurtz J M, Moras D, Rafestin-Oblin M E. Mol Endocrinol. 25 2000 August; 14(8):1210-21; Fagart J, Seguin C, Pinon O M, Rafestin-Oblin M E. Mol Pharmacol. 2005 May; 67(5):1714-22 or Hellal-Levy C, Fagart J, Souque A, Wurtz J M, Moras D, Rafestin-Oblin M E. Mol Endocrinol. 2000 August; 14(8): 1210-21. Typically, the transfection of the human mineralocorticoid receptor in COS cells together with a luciferase-expressing reporter gene allows to measure its transactivation activity in the presence of a candidate compound.

In the context of the present invention, mineralocorticoid receptor antagonists are preferably selective for the mineralocorticoid receptor as compared with the related receptors such as androgen receptor, estrogen receptors, glucocorticoid receptor, progesterone receptor, thyroid hormone receptors, peroxisome proliferator-activated receptors, retinoic acid receptor, farnesoid x receptor, pregnane x receptor, liver X receptor, vitamin D receptor, retinoid x receptor and the constitutive androstane receptor. By "selective" it is meant that the affinity of the antagonist for the mineralocorticoid receptor is at least 10-fold, preferably 25-fold, more preferably 100-fold, still preferably 500-fold higher than the affinity for the related receptors.

In one embodiment, the mineralocorticoid receptor antagonist is a low molecular weight antagonist, e.g. a small organic molecule. The term "small organic molecule" refers to a molecule of a size comparable to those organic molecules generally used in pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Da.

Typically, the mineralocorticoid receptor antagonists according to the invention generally are spirolactone-type steroidal compounds. The term "spirolactone-type" is intended to characterize a structure comprising a lactone moiety attached to a steroid nucleus, typically at the steroid "D" ring, through a spiro bond configuration. A subclass of spiro lactone-type mineralocorticoid receptor antagonist compounds consists of epoxy-steroidal mineralocorticoid receptor antagonist compounds such as eplerenone. Another subclass of spiro lactone-type antagonist compounds consists of non-epoxysteroidal mineralocorticoid receptor antagonist compounds such as spironolactone.

The epoxy-steroidal mineralocorticoid receptor antagonist compounds used in the method of the present invention generally have a steroidal nucleus substituted with an epoxy-type moiety. The term "epoxy-type" moiety is intended to embrace any moiety characterized in having an oxygen atom as a bridge between two carbon atoms.

The term "steroidal," as used in the phrase "epoxy-steroidal," denotes a nucleus provided by a cyclopentenophenanthrene moiety, having the conventional "A," "B," "C," and "D" rings. The epoxy-type moiety may be attached to the cyclopentenophenanthrene nucleus at any attachable or substitutable positions, that is, fused to one of the rings of the steroidal nucleus or the moiety may be substituted on a ring member of the ring system. The phrase "epoxy-steroidal" is intended to embrace a steroidal nucleus having one or a plurality of epoxy-type moieties attached thereto.

Epoxy-steroidal mineralocorticoid receptor antagonists suitable for use in the present methods include a family of compounds having an epoxy moiety fused to the "C" ring of the steroidal nucleus. Examples include 20-spiroxane compounds characterized by the presence of a 9α,11α-substituted epoxy moiety, such as:

Pregn-4-ene-7,21-dicarboxylic acid, 9,11-epoxy-17-hydroxy-3-oxo,γ-lactone, methyl ester, (7α,11α,17β)

Pregn-4-ene-7,21-dicarboxylic acid, 9,11-epoxy-17-hydroxy-3-oxo-, dimethyl ester, (7α,11α,17β)

3' H-cyclopropa[6,7]pregna-4,6-diene-21-carboxylic acid,9,11-epoxy-6,7-dihydro-17-hydroxy-3-oxo-,γ-lactone, (6β7β,11α,17β)

Pregn-4-ene-7,21-dicarboxylic acid, 9,11-epoxy-17-hydroxy-3-oxo,7-(1-methylethyl) ester, monopotassium salt, (7α,11α,17β)

Pregn-4-ene-7,21-dicarboxylic acid, 9,11-epoxy-17-hydroxy-3-oxo,7-methylethyl) ester, monopotassium salt, (7α,11α,17β)

3' H-cyclopropa[6,7]pregna-1,4,6-triene-21-carboxylic acid, 9,11-epoxy-6,7-dihydro-17-hydroxy-3-oxo-,γ-lactone (6β,7β,11α)

3' H-cyclopropa[6,7]pregna-4,6-diene-21-carboxylic acid, 9,11-epoxy-6,7-dihydro-17-hydroxy-3-oxo-, methyl ester, (6β,7β,11α,17β)

3' H-cyclopropa[6,7]pregna-4,6-diene-21-carboxylic acid, 9,11-epoxy-6,7-dihydro-17-hydroxy-3-oxo-, monopotassium salt, (6β,7β,11α,7β)

3' H-cyclopropa[6,7]pregna-1,4,6-triene-21-carboxylic acid, 9,11-epoxy-6,7-dihydro-17-hydroxy-3-oxo-,γ-lactone (6β,7β,11α,17β)

Pregn-4-ene-7,21-dicarboxylic acid, 9,11-epoxy-17-hydroxy-3-oxo,γ-lactone,ethyl ester, (7α,11α,17β)

Pregn-4-ene-7,21-dicarboxylic acid,9,11-epoxy-17-hydroxy-3-oxo,γ-lactone,l-methylethyl ester (7α,11α,17β)

A particular benefit of using epoxy-steroidal mineralocorticoid receptor antagonists, as exemplified by eplerenone, is the high selectivity of this group of mineralocorticoid receptor antagonists for the mineralocorticoid receptor. The superior selectivity of eplerenone results in a reduction in side effects that can be caused by mineralocorticoid receptor antagonists that exhibit non-selective binding to related receptors, such as androgen or progesterone receptors.

These epoxy steroids may be prepared by procedures described in Grob et al., U.S. Pat. No. 4,559,332. Additional processes for the preparation of 9,11-epoxy steroidal compounds and their salts are disclosed in Ng et al., WO97/21720 and Ng et al., WO98/25948.

Of particular interest is the compound eplerenone ((Pregn-4-ene-7,21-dicarboxylic acid, 9,11-epoxy-17-hydroxy-3-oxo-,γ-lactone, methyl ester, (7α,11α,17β)) (CAS No. 107724-20-9), also known as epoxymexrenone. Eplerenone is a mineralocorticoid receptor antagonist and has a higher selectivity for mineralocorticoid receptors than does, for example, spironolactone. Selection of eplerenone as the mineralocorticoid receptor antagonist in the present method would be beneficial to reduce certain side-effects such as gynecomastia that occur with use of mineralocorticoid receptor antagonists having less specificity.

Non-epoxy-steroidal mineralocorticoid receptor antagonists suitable for use in the present methods include a family of spiro lactone-type compounds defined by Formula I:

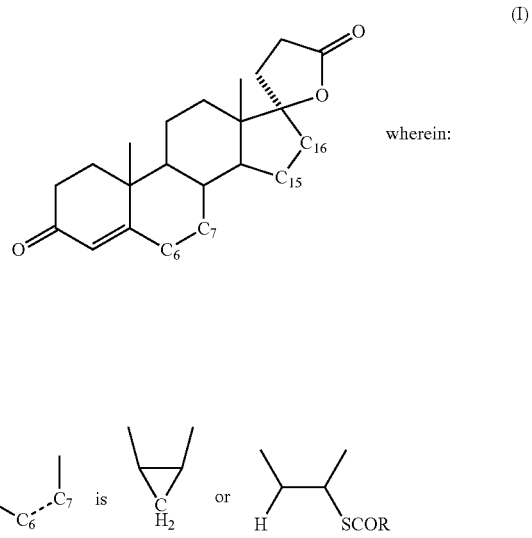

wherein:

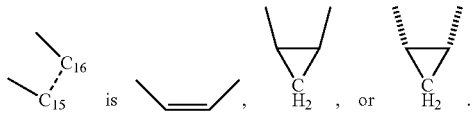

R is lower alkyl up to 5 carbon atoms, and

Lower alkyl residues include branched and unbranched groups, for example, methyl, ethyl and n-propyl.

Specific compounds of interest within Formula I are the following:

7α-acetylthio-3-oxo-4,15-androstadiene-[17(β-1')-spiro-5']-perhydrofuran-2'-one;

3-oxo-7α-propionylthio-4,15-androstadiene-[17(β-1')-spiro-5']-perhydrofuran-2'-one;

6β,7β-methylene-3-oxo-4,15-androstadiene-[17(β-1')-spiro-5']-perhydrofuran-2'-one;

15α,16α-methylene-3-oxo-4,7α-propionylthio-4-androstene[17(β-1')-spiro-5']-perhydrofuran-2'-one;

6β,7β,15α,16α-dimethylene-3-oxo-4-androstene[17(β-1')-spiro-5']-perhydrofuran-2'-one;

7α-acetylthio-15β,16β-Methylene-3-oxo-4-androstene-[17(β-1')-spiro-5']-perhydrofuran-2'-one;

15β,16β-methylene-3-oxo-7β-propionylthio-4-androstene-[17(β-1')-spiro-5']-perhydrofuran-2'-one; and 6β,7β,15β,16β-dimethylene-3-oxo-4-androstene-[17(β-1')-spiro-5']-perhydrofuran-2'-one.

Methods to make compounds of Formula I are described in U.S. Pat. No. 4,129,564 to Wiechart et al. issued on 12 Dec. 1978.

Another family of non-epoxy-steroidal compounds of interest is defined by Formula II:

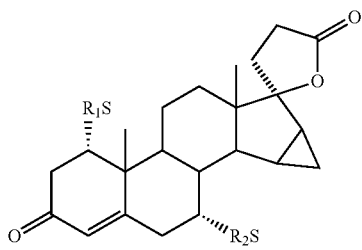

(II)

wherein R1 is C1-3-alkyl or C1-3 acyl and R2 is H or C1-3-alkyl.

Specific compounds of interest within Formula II are the following:

1α-acetylthio-15β,16β-methylene-7α-methylthio-3-oxo-17α-pregn-4-ene-21,17-carbolactone; and 15β,16β-methylene-1α,7α-dimethylthio-3-oxo-17α-pregn-4-ene-21,17-carbolactone.

Methods to make the compounds of Formula II are described in U.S. Pat. No. 4,789,668 to Nickisch et al. which issued 6 Dec. 1988.

Yet another family of non-epoxy-steroidal compounds of interest is defined by a structure of Formula III:

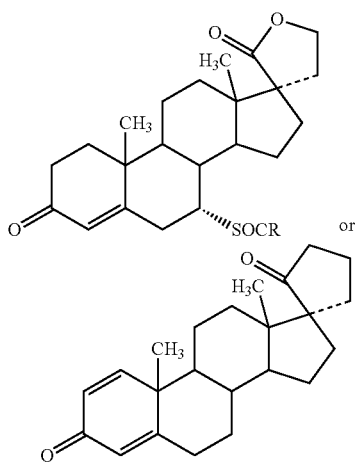

(III)

wherein R is lower alkyl, examples of which include lower alkyl groups of methyl, ethyl, propyl and butyl. Specific compounds of interest include:

3β,21-dihydroxy-17α-pregna-5,15-diene-17-carboxylic acid γ-lactone;

3β,21-dihydroxy-17α-pregna-5,15-diene-17-carboxylic acid γ-lactone 3-acetate;

3β,21-dihydroxy-17α-pregn-5-ene-17-carboxylic acid γ-lactone;

3β,21-dihydroxy-17α-pregn-5-ene-17-carboxylic acid γ-lactone 3-acetate;

21-hydroxy-3-oxo-17α-pregn-4-ene-17-carboxylic acid γ-lactone;

21-hydroxy-3-oxo-17α-pregna-4,6-diene-17-carboxylic acid γ-lactone;

21-hydroxy-3-oxo-17α-pregna-1,4-diene-17-carboxylic acid γ-lactone;

7α-acylthio-21-hydroxy-3-oxo-17α-pregn-4-ene-17-carboxylic acid γ-lactone; and

7α-acetylthio-21-hydroxy-3-oxo-17α-pregn-4-ene-17-carboxylic acid γ-lactone.

Methods to make the compounds of Formula III are described in U.S. Pat. No. 3,257,390 to Patchett which issued 21 Jun. 1966.

Still another family of non-epoxy-steroidal compounds of interest is represented by Formula IV:

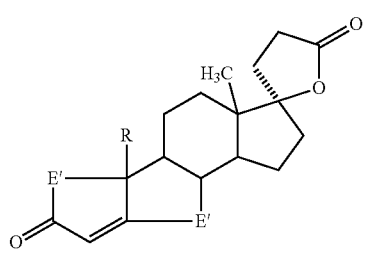

(IV)

wherein E' is selected from the group consisting of ethylene, vinylene and (lower alkanoyl)thioethylene radicals, E" is selected from the group consisting of ethylene, vinylene, (lower alkanoyl)thioethylene and (lower alkanoyl)thiopropylene radicals; R is a methyl radical except when E' and E" are ethylene and (lower alkanoyl) thioethylene radicals, respectively, in which case R is selected from the group consisting of hydrogen and methyl radicals; and the selection of E' and E" is such that at least one (lower alkanoyl)thio radical is present.

One family of non-epoxy-steroidal compounds within Formula IV is represented by Formula V:

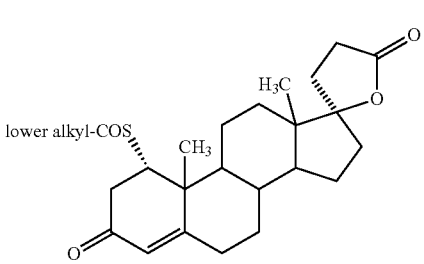

(V)

Another compound of Formula V is 1-acetylthio-17α-(2-carboxyethyl)-17β-hydroxy-androst-4-en-3-one lactone.

Another family of non-epoxy-steroidal compounds within Formula IV is represented by Formula VI:

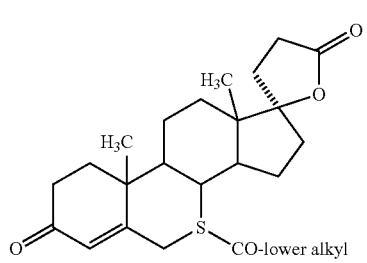

(VI)

Exemplary compounds within Formula VI include the following:

7α-acetylthio-17α-(2-carboxyethyl)-17β-hydroxy-androst-4-en-3-one lactone;

7β-acetylthio-17α-(2-carboxyethyl)-17β-hydroxy-androst-4-en-3-one lactone;
1α,7α-diacetylthio-17α-(2-carboxyethyl)-17β-hydroxy-androsta-4,6-dien-3-one lactone;
7α-acetylthio-17αe-(2-carboxyethyl)-17β-hydroxy-androsta-1,4-dien-3-one lactone;
7α-acetylthio-17α-(2-carboxyethyl)-17β-hydroxy-19-norandrost-4-en-3-one lactone; and
7α-acetylthio-17α-(2-carboxyethyl)-17β-hydroxy-6α-methylandrost-4-en-3-one lactone.

In Formulae IV-VI, the term "alkyl" is intended to embrace linear and branched alkyl radicals containing one to about eight carbons. The term "(lower alkanoyl)thio" embraces radicals of the formula lower alkyl

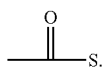

Of particular interest is the compound spironolactone (17-hydroxy-7α-mercapto-3-oxo-17α-pregn-4-ene-21-carboxylic acid γ-lactone acetate) having the following structure:

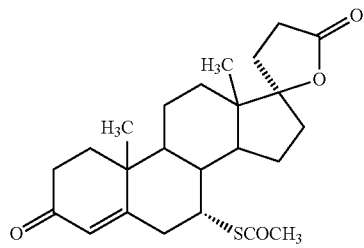

Methods to make compounds of Formulae IV-VI are described in U.S. Pat. No. 3,013,012 to Cella et al. which issued 12 Dec. 1961. Spironolactone is sold by G. D. Searle & Co., Skokie, Ill., under the trademark "ALDACTONE", in tablet dosage format doses of 25 mg, 50 mg and 100 mg per tablet.

Another family of steroidal mineralocorticoid receptor antagonists is exemplified by drospirenone, (6R-(6α,7α,8β,9α,10β,13β,14α,15α,16α,17β))-1,3',4',6,7,8,9,10,11,12,13,14,15,16,20,21-hexadecahydro-10,13-dimethylspiro[17H-dicyclopropa(6,7:15,16)cyclopenta(a)phenanthrene-17,2'(5'H)furan)-3,5'(2H)-dione, CAS registration number 67392-87-4. Methods to make and use drospirenone are described in patent GB 1550568 1979, priority DE 2652761 1976.

Crystalline forms that are easily handled, reproducible in form, easily prepared, stable, and which are non-hygroscopic have been identified for the mineralocorticoid receptor antagonist eplerenone. These include Form H, Form L, various crystalline solvates and amorphous eplerenone. These forms, methods to make these forms, and use of these forms in preparing compositions and medicaments, are disclosed in Barton et al., WO 01/41535 and Barton et al., WO 01/42272 both incorporated herein in their entirety.

Small organic molecules that may be used as mineralocorticoid receptor antagonists according to the invention may also be non-steroidal. For example, classes of non-steroidal MR antagonists have just begun to emerge over the past few years (Meyers, Marvin 11; Hu, Xiao Expert Opinion on Therapeutic Patents, Volume 17, Number 1, January 2007, pp. 17-23(7). Recently, dihydropyrymidines have been shown to display MR antagonism (Activation of Mineralocorticoid Receptors by Exogenous Glucocorticoids and the Development of Cardiovascular Inflammatory Responses in Adrenalectomized Rats. Young M J, Morgan J, Brolin K, Fuller P J, Funder I W. Endocrinology. 2010 Apr. 21). Furthermore, Arhancet el al. disclose other class of non-steroidal MR antagonists (Arhancet G B, Woodard S S, Dietz J D, Garland D J, Wagner G M, Iyanar K, Collins J T, Blinn J R, Numann R E, Hu X, Huang H C. Stereochemical Requirements for the Mineralocorticoid Receptor Antagonist Activity of Dihydropyridines. J Med Chern. 2010 Apr. 21). Other exemplary non-steroidal mineralocorticoid receptor antagonists include but are not limited to those described in US Patent Application Publication US20090163472 WO 2004/052847, WO 2008/053300 that are hereby incorporated by reference into the present disclosure. For example WO 06/076202 (published Jul. 20, 2006) reports a class of imidazole carboxamides as mineralocorticoid receptor antagonists. WO 06/012642 (published Feb. 2, 2006) reports a class of pyrrole carboxamides as mineralocorticoid receptor antagonists. WO 04/052847 (published Jun. 24, 2004) reports a class of dibenzosuberanes as mineraiocorticoid receptor antagonists. WO 05/066161 (published Jul. 21, 2005) reports a class of dibenzosuberanes as mineralocorticoid receptor antagonists. WO 03/078394 (published Sep. 25, 2003) reports a class of 3,3-bisaryl oxindoles as mineralocorticoid receptor antagonists. WO 05/097118 (published Oct. 20, 2005) reports a class of 4-aryl-1,4-dihydropyridines as mineralocorticoid receptor antagonists. WO 04/067529 (published Aug. 12, 2004) reports a class of 3-benzyl indoles as mineralocorticoid receptor antagonists. WO 06/077821 (published Jul. 27, 2006) reports classes of benzoxazinethiones and tetrahydroquinolines as mineralocorticoid receptor antagonists. WO 06/010142 (published Jan. 26, 2006) reports a class of aryl benzoxazinones/thiones as mineralocorticoid receptor antagonists.

Another example of antagonist includes a salt of the canrenoic acid. Canrenoic acid is a prodrug, which is metabolized to canrenone in the body. For intraocular administration, a salt of the canrenoic acid, such as the potassium canrenoate, may be appropriate.

Alternatively, the mineralocorticoid receptor antagonist may also consist in an antibody (the term including "antibody fragment"). In particular, the mineralocorticoid receptor antagonist may consist in an antibody directed against the mineralocorticoid receptor, in such a way that said antibody antagonizes the receptor.

Antibodies can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred. Monoclonal antibodies can be prepared and isolated using any technique that provides for the production of antibody molecules by continuous cell lines in culture. Techniques for production and isolation include but are not limited to the hybridoma technique; the human B-cell hybridoma technique; and the EBV-hybridoma technique. Alternatively, techniques described for the production of single chain antibodies (see, e.g., U.S. Pat. No. 4,946,778) can be adapted to produce anti-mineralocorticoid receptor single chain antibodies. The mineralocorticoid receptor antagonist (e.g. agonist, partial agonist or antagonist) useful in practicing the present invention also include anti-mineralocorticoid receptor antibody fragments including but not limited to F(ab')2 fragments, which can be generated by pepsin digestion of an intact antibody molecule, and Fab fragments, which can be generated by reducing the disulfide bridges of the F(ab')2 fragments. Alternatively, Fab and/or scFv expression libraries can be constructed to allow rapid identification of fragments having the desired specificity to mineralocorticoid receptor.

Humanized antibodies and antibody fragments thereof can also be prepared according to known techniques. "Humanized antibodies" are forms of non-human (e.g., rodent) chimeric antibodies that contain minimal sequence derived from non-human immunoglobulin. For the most part, humanized antibodies are human immunoglobulins (recipient antibody) in which residues from a hypervariable region (CDRs) of the recipient are replaced by residues from a hypervariable region of a non-human species (donor antibody) such as mouse, rat, rabbit or nonhuman primate having the desired specificity, affinity and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. Methods for making humanized antibodies are described, for example, by Winter (U.S. Pat. No. 5,225,539) and Boss (Celltech, U.S. Pat. No. 4,816,397).

Then after raising antibodies as above described, the skilled man in the art can easily select those antagonizing the mineralocorticoid receptor.

In another embodiment the mineralocorticoid receptor antagonist is an aptamer. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consists of a conformationally constrained antibody variable region displayed by a platform protein, such as E. coli Thioredoxin A that are selected from combinatorial libraries by two hybrid methods (Colas et al., 1996). Aptamer based on oligopeptide may fused to a penetrating sequence such asTAT or VP22 sequence.

Then after raising aptamers directed against the mineralocorticoid receptors as above described, the skilled man in the art can easily select those anatagonizing the mineralocorticoid receptor.

The present invention relates to an inhibitor of mineralocorticoid receptor gene expression for use in the treatment of fluid accumulation in and/or under the retina associated with diabetic retinopathy, glaucoma, ischemia, myopia, central serous chorioretinitis, or the exudative forms of age related macular degeneration.

Inhibitors of expression for use in the present invention may be based on antisense oligonucleotide constructs. Antisense oligonucleotides, including anti-sense RNA molecules and anti-sense DNA molecules, would act to directly block the translation of mineralocorticoid receptor mRNA by binding thereto and thus preventing protein translation or increasing mRNA degradation, thus decreasing the level of mineralocorticoid receptor, and thus activity, in a cell. For example, antisense oligonucleotides of at least about 15 bases and complementary to unique regions of the mRNA transcript sequence encoding mineralocorticoid receptor can be synthesized, e.g., by conventional phospho diester techniques and administered by e.g., intravenous injection or infusion. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732).

Small inhibitory RNAs (siRNAs) can also function as inhibitors of expression for use in the present invention. Mineralocorticoid receptor gene expression can be reduced by contacting a subject or cell with a small double stranded RNA (dsRNA), or a vector or construct causing the production of a small double stranded RNA, such that mineralocorticoid receptor gene expression is specifically inhibited (i.e. RNA interference or RNAi). Methods for selecting an appropriate dsRNA or dsRNA-encoding vector are well known in the art for genes whose sequence is known (e.g. see Tuschl, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and International Patent Publication Nos. WO 01/36646, WO 99/32619, and WO 01/68836). All or part of the phosphodiester bonds of the siRNAs of the invention are advantageously protected. This protection is generally implemented via the chemical route using methods that are known by art. The phospho diester bonds can be protected, for example, by a thiol or amine functional group or by a phenyl group. The 5'- and/or 3'-ends of the siRNAs of the invention are also advantageously protected, for example, using the technique described above for protecting the phosphodiester bonds. The siRNAs sequences advantageously comprises at least twelve contiguous dinucleotides or their derivatives.

As used herein, the term "siRNA derivatives" with respect to the present nucleic acid sequences refers to a nucleic acid having a percentage of identity of at least 90% with erythropoietin or fragment thereof, preferably of at least 95%, as an example of at least 98%, and more preferably of at least 98%.

As used herein, "percentage of identity" between two nucleic acid sequences, means the percentage of identical nucleic acid, between the two sequences to be compared, obtained with the best alignment of said sequences, this percentage being purely statistical and the differences between these two sequences being randomly spread over the nucleic acid acids sequences. As used herein, "best alignment" or "optimal alignment", means the alignment for which the determined percentage of identity (see below) is the highest. Sequences comparison between two nucleic acids sequences are usually realized by comparing these sequences that have been previously align according to the best alignment; this comparison is realized on segments of comparison in order to identify and compared the local regions of similarity. The best sequences alignment to perform comparison can be realized, beside by a manual way, by using the global homology algorithm developed by SMITH and WATERMAN (Ad. App. Math., vol. 2, p: 482, 1981), by using the local homology algorithm developed by NEDDLEMAN and WUNSCH (J. Mol. Biol., vol. 48, p: 443, 1970), by using the method of similarities developed by PEARSON and LIPMAN (Proc. Natl. Acd. Sci. USA, vol. 85, p: 2444, 1988), by using computer software using such algorithms (GAP, BESTFIT, BLAST P, BLAST N, FASTA, TFASTA in the Wisconsin Genetics software Package, Genetics Computer Group, 575 Science Dr., Madison, Wis. USA), by using the MUSCLE multiple alignment algorithms (Edgar, Robert C., Nucleic Acids Research, vol. 32, p: 1792, 2004). To get the best local alignment, one can preferably used BLAST software. The identity percentage between two sequences of nucleic acids is determined by comparing these two sequences optimally aligned, the nucleic acids sequences being able to comprise additions or deletions in respect to the reference sequence in order to get the optimal alignment between these two sequences. The percentage of identity is calculated by determining the number of identical position between these two sequences, and dividing this number by the total number of compared positions, and by multiplying the result obtained by 100 to get the percentage of identity between these two sequences.

shRNAs (short hairpin RNA) can also function as inhibitors of expression for use in the present invention.

Ribozymes can also function as inhibitors of expression for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of mineralocorticoid receptor mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUc. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable.

Both antisense oligonucleotides and ribozymes useful as inhibitors of expression can be prepared by known methods. These include techniques for chemical synthesis such as, e.g., by solid phase phosphoramadite chemical synthesis. Alternatively, antisense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Antisense oligonucleotides, siRNAs, shRNAs and ribozymes of the invention may be delivered in vivo alone or in association with a vector. In its broadest sense, a "vector" is any vehicle capable of facilitating the transfer of the antisense oligonucleotide, siRNA, shRNA or ribozyme nucleic acid to the cells and preferably cells expressing mineralocorticoid receptor. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide, siRNA, shRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rous sarcoma virus; adenovirus, adeno-associated virus; SV 40-type viruses; polyoma viruses; Epstein-Barr viruses; papilloma viruses; herpes virus; vaccinia virus; polio virus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high efficiency transduction of genes in vivo. Standard protocols for producing replication deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, 1990 and in Murry, 1991).

Preferred viruses for certain applications are the adenoviruses and adeno-associated (AAV) viruses, which are double-stranded DNA viruses that have already been approved for human use in gene therapy. Actually 12 different AAV serotypes (AAVI to 12) are known, each with different tissue tropisms (Wu, Z Mol Ther 2006; 14:316-27). Recombinant AAV are derived from the dependent parvovirus AAV2 (Choi, V W J Virol 2005; 79:6801-07). The adeno-associated virus type 1 to 12 can be engineered to be replication deficient and is capable of infecting a wide range of cell types and species (Wu, Z Mol Ther 2006; 14:316-27). It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g. Sambrook et al., 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUCI8, pUCI9, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

In a preferred embodiment, the antisense oligonucleotide, siRNA, shRNA or ribozyme nucleic acid sequence is under the control of a heterologous regulatory region, e.g., a heterologous promoter. The promoter may be specific for Müller glial cells, microglia cells, endothelial cells, pericyte cells and astrocytes. For example, a specific expression in Müller glial cells may be obtained through the promoter of the glutamine synthetase gene is suitable. The promoter can also be, e.g., a viral promoter, such as CMV promoter or any synthetic promoters.

Furthermore, the inventors believe that anti-edematous effects of corticosteroid on the retina are mainly explained by an action via MR pathway, more than by an action on GR pathway. The inventors have indeed observed that administration of a glucocorticoid (e.g. triamcinolone acetonide) provides the same effect as a MR antagonist on AQP4 expression. Accordingly, MR antagonists would synergize the effects of glucocorticoids in the treatment of fluid accumulation in and/or under the retina, but also would prevent the severe side effects of glucocorticoids.

Thus a further aspect of the invention relates to a combination of a glucocorticoid and a MR antagonist or an inhibitor of mineralocorticoid receptor gene expression for use in the treatment of fluid accumulation in and/or under the retina associated with diabetic retinopathy, glaucoma, ischemia, myopia, central serous chorioretinitis, or the exudative forms of age related macular degeneration.

The combination of an MR antagonist and a glucocorticoid potentiates the effect of the glucocorticoids and allows to reduce the doses of glucocorticoids, thereby limiting their adverse side effects.

As used herein the term "glucocorticoid" has it general meaning in the art and refers to compounds that bind and activate the glucocorticoid receptor (GR) also known as NR3C1 (nuclear receptor subfamily 3, group C, member 1).

The glucocorticoids that may be used according to the invention include, but are not limited to, 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluoromethalone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, anecortave acetate, and any of their derivatives.

The present also relates to a pharmaceutical composition (as herein after described) comprising an amount of at least one glucocorticoid and an amount of at least one MR antagonist or an inhibitor of mineralocorticoid receptor gene expression for use in the treatment of fluid accumulation in and/or under the retina associated with diabetic retinopathy, glaucoma, ischemia, myopia, central serous chorioretinitis, or the exudative forms of age related macular degeneration.

The present invention also relates to a kit comprising at least one glucocorticoid and at least one MR antagonist or an inhibitor of mineralocorticoid receptor gene expression for use in the treatment of fluid accumulation in and/or under the retina associated with diabetic retinopathy, glaucoma, ischemia, myopia, central serous chorioretinitis, or the exudative forms of age related macular degeneration.

The present invention also relates to an MR antagonist or an inhibitor of mineralocorticoid receptor gene expression for use in the prevention of the side effects induced by glucocorticoid during the treatment of fluid accumulation in and/or under the retina associated with diabetic retinopathy, glaucoma, ischemia, myopia, central serous chorioretinitis, or the exudative forms of age related macular degeneration.

Finally, the inventors believe that MR agonists or glucocorticoids capable of transactivating the MR may be useful for the treatment of fluid accumulation in and/or under the retina resulting from a loss of AQP4 expression associated with uveitis, retinitis pigmentosa, or retinal cytotoxic or neurotoxic edemas.

Accordingly, the present invention relates to a MR agonist for use in the treatment of fluid accumulation in and/or under the retina associated with uveitis or retinitis pigmentosa or retinal cytotoxic or neurotoxic edemas.

As used herein, the term "mineralocorticoid receptor (MR) agonist" is a natural or synthetic compound which binds the mineralocorticoid receptor to activate said mineralocorticoid receptor site for initiating a pathway signalling and further biological processes.

Typically, MR agonist is aldosterone or an analog thereof. As used herein, the term "analog" refers to an agent that is structurally similar to another, but differs slightly in composition, for example the replacement of one atom by an atom of a different element or functional group. For example, an analog of aldosterone is fludrocortisone that is 9-fluoro-11,17-dihydroxy-17-(2-hydroxyacetyl)-10,13-dimethyl-1,2,6,7,8,9,10,11,12,13,14,15,16,17-tetradecahydro-cyclopenta[a]phenanthren-3-one.

According to the invention, the active ingredients of the invention (e.g. MR antagonist or agonists) are administered to the subject in a therapeutically effective amount.

By a "therapeutically effective amount" is meant a sufficient amount of the active ingredient to treat fluid accumulation in and/or under the retina at a reasonable benefit/risk ratio applicable to any medical treatment.

It will be understood that the total daily usage of the compounds and compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

As used herein, the term "subject" denotes a mammal, such as a rodent, a feline, a canine, and a primate. Preferably, a subject according to the invention is a human.

The active ingredients of the invention (e.g. MR antagonist or agonists) may be combined with pharmaceutically acceptable excipients, and optionally sustained-release matrices, such as biodegradable polymers, to form pharmaceutical compositions.

The term "Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

In the pharmaceutical compositions of the present invention, the active ingredients of the invention can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

Preferably, local ocular routes should be used such as intravitreous, topical, periocular injections (sub conjuntival, peri bulbar, latero bulbar, retro bulbar, sub tenon, supra choroidal), intra or peri ocular implants (intra scleral, peri scleral, episcleral), intra vitreous implants or supra choroidal implants or particles or polymeric composition, or any releasing systems such as emulsions, solid non-biodegradable or degradable implants or tablets, mini pumps or any topical formulations.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria, virus and fungi.

Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The active ingredients of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active ingredients of the invention in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

In addition to the active ingredients of the invention formulated for parenteral administration, such as intravenous or intramuscular injection, other pharmaceutically acceptable forms include, e.g. tablets or other solids for oral administration; liposomal formulations; time release capsules; and any other form currently used.

Active ingredient may be also delivered directly to the eye by ocular tissue injection such as periocular, conjunctival, subtenon, intracameral, intravitreal, intraocular, subretinal, subconjunctival, retrobulbar, suprachoroidal or intracanalicular injections; by direct application to the eye using a catheter or other placement device such as a retinal pellet, intraocular insert, suppository or an implant comprising a porous, non-porous, or gelatinous material; by topical ocular drops or ointments; or by a slow release device in the cul-de-sac or implanted adjacent to the sclera (trans scleral) or in the sclera (intrascleral) or supra choroidal or within the eye. Intracameral injection may be through the cornea into the anterior chamber to allow the agent to reach the trabecular meshwork. Intracanalicular injection may be into the venous collector channels draining Schlemm's canal or into Schlemm's canal.

For ophthalmic delivery, an active ingredient may be combined with ophthalmologically acceptable preservatives, co-solvents, surfactants, viscosity enhancers, penetration enhancers, buffers, sodium chloride, or water to form an aqueous, sterile ophthalmic suspension or solution. Solution formulations may be prepared by dissolving the active ingredient in a physiologically acceptable isotonic aqueous buffer. Further, the solution may include an acceptable surfactant to assist in dissolving the active ingredient. Viscosity building agents, such as hydroxymethyl cellulose, hydroxyethyl cellulose, methylcellulose, polyvinylpyrrolidone, or the like may be added to the compositions of the present invention to improve the retention of the compound.

In order to prepare a sterile ophthalmic ointment formulation, the active ingredient is combined with a preservative in an appropriate vehicle, such as mineral oil, liquid lanolin, or white petrolatum. Sterile ophthalmic gel formulations may be prepared by suspending the active ingredient in a hydrophilic base prepared from the combination of, for example, CARBOPOL®-940 (BF Goodrich, Charlotte, N.C.), or the like, according to methods known in the art. VISCOAT® (Alcon Laboratories, Inc., Fort Worth, Tex.) may be used for intraocular injection, for example. Other compositions of the present invention may contain penetration enhancing agents such as cremophor and TWEEN® 80 (polyoxyethylene sorbitan mono laureate, Sigma Aldrich, St. Louis, Mo.), in the event the active ingredient is less penetrating in the eye.

In a particular embodiment, the pharmaceutical composition of the invention is an ophthalmic drop formulation. The eye drop is provided in any formulation generally used, for example, in the form of an aqueous eye drop such as aqueous eye drop solution, aqueous eye drop suspension, viscous eye drop solution, solubilized eye drop solution and the like, or in the form of a non-aqueous eye drop such as a non-aqueous eye drop solution, non-aqueous eye drop suspension and the like. When the composition the present invention is prepared as an aqueous eye drop, it preferably contains an additive which is usually used in an aqueous eye drop. The examples of such an additive include preservatives, isotonic agents, buffering agents, stabilizer, pH regulators or the like.

In another particular embodiment, the active ingredients of the invention are delivered through a biodegradable ocular implant.

The implants can be formed in manner that the active ingredient is homogenously distributed or dispersed throughout the biodegradable polymer matrix. Additionally, the implants can be formed to release the active ingredient into an ocular region of the eye over various time periods. Thus, the active ingredient can be released from implants made according to the present invention for a period of time of, for example, 30-200 days.

The active ingredient can comprise from about 10% to about 90% by weight of the implant. In one variation, the agent is from about 40% to about 80% by weight of the implant. In a preferred variation, the agent comprises about 60% by weight of the implant.

In a particular embodiment, the active ingredient can be homogeneously dispersed in the biodegradable polymer of the implant. The implant can be made, for example, by a sequential or double extrusion method. The selection of the biodegradable polymer used can vary with the desired release kinetics, patient tolerance, the nature of the disease to be treated, and the like. Polymer characteristics that are considered include, but are not limited to, the biocompatibility and biodegradability at the site of implantation, compatibility with the active ingredient of interest, and processing temperatures. The biodegradable polymer matrix usually comprises at least about 10, at least about 20, at least about 30, at least about 40, at least about 50, at least about 60, at least about 70, at least about 80, or at least about 90 weight percent of the implant. In one variation, the biodegradable polymer matrix comprises about 40% to 50% by weight of the implant.

Biodegradable polymers which can be used include, but are not limited to, polymers made of monomers such as organic esters or ethers, which when degraded result in physiologically acceptable degradation products. Anhydrides, amides, orthoesters, or the like, by themselves or in combination with other monomers, may also be used. The polymers are generally condensation polymers. The polymers can be crosslinked or non-crosslinked. If crosslinked, they are usually not more than lightly crosslinked, and are less than 5% crosslinked, usually less than 1% crosslinked.

Of particular interest are polymers of hydroxyaliphatic carboxylic acids, either homo- or copolymers, and polysaccharides. Included among the polyesters of interest are homo- or copolymers of D-lactic acid, L-lactic acid, racemic lactic acid, glycolic acid, caprolactone, and combinations thereof. Copolymers of glycolic and lactic acid are of particular interest, where the rate of biodegradation is controlled by the ratio of glycolic to lactic acid. The percent of each monomer in poly(lactic-co-glycolic)acid (PLGA) copolymer may be 0-100%, about 15-85%, about 25-75%, or about 35-65%. In certain variations, 25/75 PLGA and/or 50150 PLGA copolymers are used. In other variations, PLGA copolymers are used in conjunction with polylactide polymers or polyurethanes.

Other agents may be employed in the formulation for a variety of purposes. For example, buffering agents and preservatives may be employed. Preservatives which may be used include, but are not limited to, sodium bisulfite, sodium bisulfate, sodium thiosulfate, benzalkonium chloride, chlorobutanol, thimerosal, phenylmercuric acetate, phenylmercuric nitrate, methylparaben, polyvinyl alcohol and phenyl ethyl alcohol. Examples of buffering agents that may be employed include, but are not limited to, sodium carbonate, sodium borate, sodium phosphate, sodium acetate, sodium bicarbonate, and the like, as approved by the FDA for the desired route of administration. Electrolytes such as sodium chloride and potassium chloride may also be included in the formulation.

The biodegradable ocular implants can also include additional hydrophilic or hydrophobic compounds that accelerate or retard release of the active ingredient. Additionally, release modulators such as those described in U.S. Pat. No. 5,869,079 can be included in the implants. The amount of release modulator employed will be dependent on the desired release profile, the activity of the modulator, and on the release profile of the active ingredient in the absence of modulator. Where the buffering agent or release enhancer or modulator is hydrophilic, it may also act as a release accelerator. Hydrophilic additives act to increase the release rates through faster dissolution of the material surrounding the drug particles, which increases the surface area of the drug exposed, thereby increasing the rate of drug diffusion. Similarly, a hydrophobic buffering agent or enhancer or modulator can dissolve more slowly, slowing the exposure of drug particles, and thereby slowing the rate of drug diffusion.

The release kinetics of the implants of the present invention can be dependent in part on the surface area of the implants. A larger surface area exposes more polymer and active ingredient to ocular fluid, causing faster erosion of the polymer matrix and dissolution of the active ingredient particles in the fluid. Therefore, the size and shape of the implant may also be used to control the rate of release, period of treatment, and active ingredient concentration at the site of implantation. At equal active ingredient loads, larger implants will deliver a proportionately larger dose, but depending on the surface to mass ratio, may possess a slower release rate. For implantation in an ocular region, the total weight of the implant preferably ranges, e.g., from about 200-15000 [mu]g, usually from about 1000-5000 [mu]g. In one variation, the total weight of the implant is about 1200 to about 1,800 [mu]g. In another variation, the total weight of the implant is about 2400 to about 3,600 [mu]g. Preferably, the implant has a weight between about 100 [mu]g and about 2 mg.

The implants of the invention are typically solid, and may be formed as particles, sheets, patches, plaques, films, discs, fibers, rods, and the like, or may be of any size or shape compatible with the selected site of implantation, as long as the implants have the desired release kinetics and deliver an amount of active ingredient that is therapeutic for the intended medical condition of the eye. The upper limit for the implant size will be determined by factors such as the desired release kinetics, toleration for the implant at the site of implantation, size limitations on insertion, and ease of handling. For example, the vitreous chamber is able to accommodate relatively large rod-shaped implants, generally having diameters of about 0.05 mm to 3 mm and a length of about 0.5 to about 10 mm. In one variation, the rods have diameters of about 0.1 mm to about 1 mm. In another variation, the rods have diameters of about 0.3 mm to about 0.75 mm. In yet a further variation, other implants having variable geometries but approximately similar volumes may also be used.

The biodegradable implants can be inserted into the eye by a variety of methods, including placement by forceps, by trocard, or by other types of applicators, after making an incision in the sclera. In some instances, a trocard or applicator may be used without creating an incision. In a preferred variation, a hand held applicator is used to insert one or more biodegradable implants into the eye. The hand held applicator typically comprises an 18-30 GA stainless steel needle, a lever, an actuator, and a plunger. Suitable devices for inserting an implant or implants into a posterior ocular region or site includes those disclosed in U.S. patent application Ser. No. 10/666,872.

The invention will be further illustrated by the following examples and figures. However, these examples should not be interpreted in any way as limiting the scope of the present invention.

EXAMPLE 1

The Neuroretina is a Novel Mineralocorticoid Target: Aldosterone Up-Regulates Ion and Water Channels in Müller Glial Cells Abstract 5 Glucocorticoids (G) reduce diabetic macular edema, but the mechanisms underlying G effects are imperfectly elucidated. G may bind to glucocorticoid (GR) and mineralocorticoid (MR) receptors. We hypothesize that MR activation may influence retinal hydration. The effect of the MR agonist aldosterone (24 hrs) on ion/water channels expression (real-time PCR, western blot, immunofluorescence) was investigated on cultured retinal Müller glial cells (RMG, that contribute to fluid homeostasis in the retina), in Lewis rat retinal explants and in retinas from aldosterone injected eyes. We evidenced cell-specific expression of MR, GR and II-beta hydroxysteroid dehydrogenase type II. Aldosterone significantly enhances expression of sodium and potassium channels ENaC-a (6.5 fold) and Kir4.1 (1.9 fold) through MR and GR occupancy, while aquaporin 4 (AQP4, 2.9 fold) up-regulation is MR-selective. Aldosterone intravitreous injection induces retinal swelling (24% increase compared to sham-injected eyes) and activation of RMG. It promotes additional localization of Kir4.1 and AQP4 towards apical microvilli of RMG. Our results highlight the mineralocorticoid-sensitivity of the neuroretina and show that aldosterone controls hydration of the healthy retina through regulation of ion/water channels expression in RMG. These results provide a rationale for future investigations of abnormal MR signalling in the pathologic retina.

Introduction

Ion channels and aquaporins are differentially expressed in retinal cells, and play important roles in ion and water movements that are crucial for adequate control of retinal hydration. Particularly, retinal Müller glial cells (RMG) are key elements for the control of retina hydration and homeostasis of potassium, as they establish an anatomical and functional connection between the retinal neurons and the retinal blood vessels on one hand, and with the vitreous and the subretinal space on the other hand. Any alteration in the retinal dehydration processes leads to retinal edema.

High doses of corticosteroids are currently injected into the vitreous cavity of patients with macular edema because of their anti-inflammatory and anti-edematous effects on the retina, but are associated with frequent and sometimes severe side effects as intraocular hypertension or toxicity due to reduction of retinal cell viability through paraptosis. The molecular mechanisms underlying the effects of glucocorticoids in the eye remain largely unknown, in as much as glucocorticoid hormones act through binding to the glucocorticoid receptor (OR) and also to the mineralocorticoid receptor (MR). In fact the MR has similar high affinity for aldosterone and for glucocorticoid hormones that largely prevail in the plasma. Permanent occupancy of the MR by circulating glucocorticoids is prevented to a large extent by the metabolizing enzyme Il-beta hydroxysteroid dehydrogenase type II (HSD2) in mineralocorticoid-sensitive tissues that co-express MR and HSD2. Both OR and MR are ligand-dependent transcription factors that belong to the nuclear receptor superfamily. Whilst GR exerts pleiotropic effects on cell homeostasis and metabolism, the MR is classically involved in the regulation of renal sodium reabsorption. Indeed, the aldosterone/MR pathway upregulates the activity of the epithelial sodium channel (ENaC) in the kidney collecting duct, through a complex cascade of events and also favors potassium excretion through regulation of K channels.

The progressive identification of novel MR target tissues (heart, vessels, brain, skin, adipocytes, macrophages . . . ) unraveled unexpected roles of this receptor. Interestingly, in the eye, the MR is also expressed but information on its biological activity and potential clinical relevance is lacking. Particularly in the retina, the functions and cell-specific expression of MR, OR and HSD2 are far from being completely established. Whether and how corticosteroid hormones and particularly aldosterone contribute to homeostasis of normal retina is currently undetermined. We hypothesized that MR may be involved in retinal fluid homeostasis.

In this context, this study was designed to document the response to aldosterone (24 hrs) as a regulator of ion and water channels. We show that MR, OR and HSD2 are co-expressed in the rat neuroretina. We found that the acute intraocular aldosterone injection increases the retinal thickness, presumably through fluid accumulation in the neuroretina. In RMO, aldosterone up-regulates the expression of the inward rectifying potassium channel Kir4.1 and of the a subunit of ENaC through MR and mainly GR activation, while aquaponn 4 (AQP4) IS specifically up-regulated by the aldosterone/MR pathway. Aldosterone also favors localization of Kir4.1 and AQP4 towards the apical microvilli of Müller cells. Taken together, our results demonstrate that the neuroretina and more specifically RMG cells are novel targets of aldosterone. The hormone may therefore be considered as a novel player in the regulation of healthy retinal homeostasis and hydration.

Materials and Methods

Animals:

All experiments were performed in accordance with the European Communities Council Directive 86/609/EEC and approved by local ethical committees. Adult female Lewis rats (8-12 weeks old, Janvier, Le Genest-Saint-Isle, France) were used for preparation of RMG primary cultures, for retinal organotypic cultures and for in vivo experiments. Rats were sacrificed by carbon dioxide inhalation.

Rat RMG Primary Culture:

Rat RMG cells were obtained as described (deKozak, Y., Naud, M. C., Bellot, J., Faure, J. P., and Hicks, D. (1994) Differential tumor necrosis factor expression by resident retinal cells from experimental uveitis-susceptible and -resistant rat strains. J Neuroimmunol 55, 1-9). Briefly, rats at postnatal (PN) day 17 (when RMG cells are mature) were sacrificed and eyes enucleated. Intact eyeballs were maintained in DMEM overnight at room temperature in the dark, and then incubated 45 min with 2 mg/ml trypsin/collagenase I at 37° C. The neural retinas were separated from the lens and vitreous, cut into small fragments and plated in Petri dishes containing DMEM supplemented with 10% FCS, 100 units/ml penicillin, 100 mug/ml streptomycin, and 0.2% amphotericin B. Cultures were maintained at 37° C. in a humidified atmosphere containing 5% CO2. After 5 to 6 days, the cultures were washed extensively with medium so that only a strongly adherent flat cell population remained.

Corticosteroid Treatments of Cultured Cells:

Müller cells were seeded in 6-well tissue culture plates (Becton Dickinson, Le Pont de Claix, France). Rat PN17 RMG cells were maintained in their initial Petri dishes. Sub confluent (80%) cells were incubated in media supplemented with 10% steroid-free (charcoal treated) FCS for 24 hrs. Corticosteroid (Sigma-Aldrich, Saint Quentin Fallavier, France) treatments were then applied respectively for a further 24 hrs: 10 nM aldosterone, 10 nM aldosterone plus 1).IM RU38486 (GR-specific antagonist), 10 nM aldosterone plus 1 muM RU26752 (MR-specific antagonist) or 1 muM dexamethasone. The steroids were previously dissolved in 2% steroid-free FCS media containing 0.1% ethanol. Control cells were treated with 0.1% ethanol in media. Addition of the antagonists alone (i.e. in the absence of aldosterone) was also performed on Müller cells and did not induce the expression of the analyzed genes.

Rat Retinal Explant:

After enucleation, rat retinas were isolated immediately under aseptic conditions and cut into 4 pieces. They were then transferred onto a Cyclopore 0.2).Im polycarbonate membrane (Whatman, Maidstone, England), and flat-mounted with the vitreal side up. The support membranes were placed in 6-well tissue culture plates containing 2 ml DMEM supplemented with 10% steroid-free FCS, 1% penicillin-streptomycin and 0.1% amphotericin B. Explants were treated with corticosteroids as described for cultured cells. Similarly, the dose-dependent effect of aldosterone (0.1-100 nM) was analyzed on retinal explants in separate experiments.

Reverse Transcription and Real-Time PCR:

Total RNA was isolated from the treated RMG cells and retinal explants using RNeasy Mini Kit (Qiagen, Courtaboeuf, France). First-strand cDNA was synthesized after DNase I (Qiagen) treatment using random primers (Invitrogen) and superscript II reverse transcriptase (Invitrogen). Transcript levels of ENaC-a, Kir4.1 and AQP4 were analyzed by real-time PCR performed in 7500 Real-Time PCR System (Applied Biosystems, Foster City, Calif., USA) with either TaqMan® (Applied Biosystems) or SYBR® Green (Invitrogen, Cergy Pontoise, France) detection. The 18S was used as internal control.

Western Blot:

Retinal explants were homogenized in Np40 buffer in the presence of protease inhibitors. The protein concentration was determined by the Bradford method. Equal amounts of protein (12 .ug) were separated on Novex® 4%-12% Tris-Glycine gel (Invitrogen), transferred to nitrocellulose, and the blots were incubated with primary antibodies at 4° C. overnight. The membranes were washed, incubated with horse radish peroxidase conjugated goat anti-rabbit IgG (1:3000, Vector, AbCys, Paris, France) for 1 hr at room temperature, and developed using ECL Plus western blotting detection reagents (GE healthcare, Orsay, France). The j3-actin was used as internal control. The following primary antibodies were used: rabbit anti-alpha ENaC (1:500, Abcam, Cambridge, Mass., USA), rabbit anti-Kir4.1 (1:400, Alomone Labs, Jerusalem, Israel), rabbit anti-AQP4 (1:750, Millipore, St Quentin en Yvelines, France) and rabbit anti-j3-actin (1:1000, Abcam)

Intravitreous Injection in Rat Eyes:

Anesthesia of rats was induced by intramuscular injection of ketamine (100 mg/kg, Virbac, Carros, France) and chlorpromazine (0.65 mg/kg, LARGACTIL®, Sanofi Aventis, Livron sur Drome, France). Intravitreous injections were performed using microfine (300 µl) syringes with 30 G needles under topical anesthesia (tetracaine 1%, Aldrich, Lyon, France). Rat eyes were injected with 5 µl aldosterone diluted in 0.9% saline to obtain a concentration of 200 nM for injection, corresponding to a final concentration of 20 nM in the vitreous. Control rat eyes were injected with 5 µl saline. Twenty-four hrs after injection, rats were sacrificed. Eyes were then removed for retinal flat mounting, immunohistochemistry and morphological analysis respectively.

Retinal Flat Mounting:

Eyes were fixed for 15 min in 4% paraformaldehyde (PFA, LADD, Inland Europe, Conflans-sur-Lanterne, France). After washing, retinas were isolated, cut by 4 orthogonal incisions and post-fixed with acetone 100% at −20° C. for 15 min. They were then rehydrated with phosphate-buffered saline (PBS) containing 1% Triton X-I00, and incubated with a polyclonal rabbit antibody against AQP4 (1:100) or a polyclonal rabbit antibody against glial fibrillary acidic protein (GF AP, 1:100, Dako, Trappes, France) at room temperature under stirring overnight. After washing with PBS, an Alexa Fluor 488-conjugated goat anti-rabbit IgG (1:100, Molecular Probes, Leiden, Netherlands) was applied for 1 hr. Blood vessels were stained with TRITC labeled lectin from Bandeiraea simplicifolia BS-1 (1:100, SigmaAldrich). The retinas were flat mounted using gel mount (Biomeda Corp., VWR, Fontenay-sous-Bois, France). Images were taken using a confocal laser scanning microscope Zeiss LSM 710 (Oberkochen, Germany).

Immunofluorescence:

Eyes were snap frozen in Tissue-Tek OCT-compound (Bayer Diagnostics, Puteaux, France). Ten µm cryostat sections of rat eyes were fixed in 4% PFA for 15 min and permeabilized with 0.1% Triton X-I00 for 30 min. Unspecific binding sites were blocked with 5% normal goat serum for 1 hr. The sections were then incubated with primary antibodies for 1 hr at room temperature, washed in PBS, and further incubated with secondary antibodies for 1 hr. After washing, slides were stained for 5 min with 4',6-Diamidino-2-Phenyl-Indole (DAPI, 1:3000, SigmaAldrich), washed again, and mounted with gel mount. Control sections were stained without primary antibodies. Images were taken using a fluorescence microscope (Olympus BX51, Rungis, France) equipped with a CCD camera (Olympus DP70). The following antibodies were used: rabbit anti-alpha ENaC (1:100), rabbit anti-Kir4.1 (1:200), rabbit anti-AQP4 (1:200), Alexa Fluor 488-coupled goat anti-rabbit IgG (1:200), and Alexa Fluor 596-coupled goat anti-rabbit IgG (1:200, Molecular Probes).

Immunohistochemistry:

Enucleated eyes were fixed in 4% PFA for 2 hours, dehydrated and embedded in paraffin. Ten µm sections were deparaffinized in xylene, hydrated in a graded alcohol series, and washed in PBS-Tween (PBST). After antigen retrieval by heating in citrate buffer and inactivation of endogenous peroxidase by 3% $H_2O_2$, sections were incubated with 3% normal horse serum or a blocking buffer in the Tyramide Signal Amplification (TSA) kit (Perkin Elmer, Courtaboeuf, France) to reduce the nonspecific signal. The primary antibodies were applied overnight at 4° C. After washing in PBST, sections were incubated with the biotinylated secondary antibodies for 45 min at room temperature. Amplification of the signal was obtained with TSA kit or VECTASTAIN ABC kit (Vector) according to the manufacturer's instructions. Signal was revealed with 3,3'-diaminobenzidine tetrahydrochloride (Dako). Rat renal sections were used as positive controls. Negative controls were performed without primary antibodies. The following antibodies were used: mouse monoclonal anti-MR 6G 1 (1:100, kindly provided by C. Gomez-Sanchez, Division of Endocrinology, University of Mississippi Medical Center, Jackson, Miss.), sheep anti-I1f3 HSD2 (1:2000, Millipore), rabbit anti-GR (1:2000, Santa Cruz, Heidelberg, Germany), rabbit anti-alpha ENaC (1:200), biotinylated horse anti-mouse IgG BA2000 (1:250, Vector), biotinylated rabbit anti-sheep IgG BA6000 (1:400, Vector), and biotinylated goat anti-rabbit IgG BA1 000 (1:500, Vector).

Morphology:

Enucleated eyes were fixed in 2.5% glutaraldehyde in cacodylate buffer (0.1 M, pH 7.4). After 30 min, eyes were dissected at the level of the limbus and lens removed. The posterior part was fixed for a further 5 hrs, dehydrated in a graded alcohol series (50%, 70%, 95% and 100%) and embedded in epoxy resin. Semi-thin sections (1 J.lm) were cut using an ultramicrotome (Reichert Ultracut E, Leica, Wetzlar, Germany), and stained with toluidine blue. The morphology was examined under a light microscope (DMRB, Leica). Retinal thickness was measured manually every 100 µm from the peripheral to the posterior pole. For analysis, the retina was divided into 3 zones: periphery, middle and posterior pole. In each zone, 3-4 individual measurements were performed in each section. Two to 6 sections were analyzed per rat (3 rats with aldosterone intravitreous injection and 3 with sham injection)

Statistics:

Data were expressed as means±SE. Statistical analysis was made using the Graphpad Prism5 program (Graphpad Software, San Diego, Calif., USA). Student t-test was used for two groups, one way ANOV A test followed by Bonferroni's comparison for multiple groups. $P<0.05$ deemed significant.

Results

MR, GR and HSD2 are Co-Expressed in Retinal Cells:

As a prerequisite to search for aldosterone-dependent effects, corticosteroid receptor expression has been evaluated in the rat retina (the different zones of the retina are provided in a semi-thin section of a normal rat retina for comprehension). We found that the GR is expressed in several zones of the retina and that the MR is also expressed in the same regions of the retina, i.e. in the nuclei of ganglion cells (ganglion cell layer, GCL) and of cells in the inner nuclear layer (INL) that contains bipolar cells, amacrine cells, horizontal cells and RMG cells. Nuclei of RMG cells are mostly located in the central part of the INL. To assess the specificity of retinal MR immunohistochemistry, the MR antibody was used on kidney sections, showing immunolabeling restricted to the distal nephron, as expected. The MR-protector enzyme HSD2 has similar localization as the MR, in ganglion cells and cells of the INL, as well as in the distal nephron, provided as a positive control. Although immunohistochemistry is not a quantitative method, the comparable intensity of MR and HSD2 labeling in retina and in kidney collecting ducts suggests that their significant level of expression in the eye should fully allow aldosterone/MR-specific effects as it does in the kidney.

Aldosterone Induces Intraretinal Fluid Accumulation:

A single injection of aldosterone (20 nM) in the vitreous cavity of Lewis rats induces retinal morphological changes 24 hrs later. Examination of semi-thin sections shows fluid accumulation in the entire retina, especially in between nuclei of the outer nuclear layer (ONL) as compared to sham-injected retina. RMO cell prolongations apical processes or their surrounding extra-cellular spaces appeared swollen. Retinal thickness is significantly increased in aldosterone-injected eyes compared to sham-injected ones.

Aldosterone Enhances Glial Activation:

GFAP is an intermediated filament protein present in the RMG and in the astrocytes of the retina. Its up-regulation is an early event under retinal stress conditions. Aldosterone enhances glial activation as suggested by GFAP distribution along RMG cells prolongations in aldosterone-injected retinas as compared to sham-injected retinas. In sham-injected retinas, GFAP is expressed mostly at the end feet of RMG and in astrocytes in the nerve fiber layer (NFL). In aldosterone-injected retinas, GFAP immunostaining is enhanced in the NFL and extends all along RMG prolongations up to apical processes at the outer limiting membrane (OLM).

Aldosterone and Dexamethasone Up-Regulate ENaC-α in RMG Cells:

The sodium channel ENaC is a main mineralocorticoid target in renal collecting duct cells that transport sodium. We found that ENaC is expressed in retinal cells, and its expression is regulated by corticosteroids. Aldosterone (10 nM for 24 hrs) induces a significant up-regulation of ENaC-α subunit mRNA expression in rat RMO primary cultures and in rat retinal explants. The increase in ENaC-α subunit transcripts is inhibited by both the MR (RU26752) and OR (RU38486) antagonists indicating that the aldosterone-induced ENaC-α up-regulation is both MR- and mostly GR-dependent. This is further confirmed by the efficiency of the glucocorticoid agonist dexamethasone to increase ENaC-α expression. Aldosterone increases ENaC-α transcripts in a dose dependent manner; its expression at the protein level is also up-regulated and the aldosterone-induced ENaC protein is not reduced in the presence of the MR antagonist RU 26752.

The immunolocalization of ENaC on retina from saline-injected rats shows that ENaC-α is expressed in cells in the INL with some localizations at the cell membrane. In aldosterone-injected eyes, the intensity of ENaC-α expression and the number of cells expressing ENaC-α is increased in the INL. Control experiments using the same ENaC antibody on kidney sections (peroxidase immunohistochemistry) confirms the specificity of ENaC-α labeling restricted to the collecting duct, whilst histochemistry without first antibody is negative.

Aldosterone and Dexamethasone Control the Expression of the Potassium Channel Kir4.1 in the Retina:

Kir4.1 is considered as the major potassium channel in RMG cells and its expression pattern has been documented. In rat RMG primary cultures and in retinal explants, both aldosterone and dexamethasone up-regulate Kir 4.1; the GR antagonist RU38486 is fully efficient to reduce it, while the MR antagonist has weaker (or no) effect. Dose-dependent increase in transcripts appears fully saturated at 10 nM aldosterone. Channel expression at the protein level is also up-regulated by aldosterone; aldosterone-induced Kir4.1 protein is reduced in the presence of the MR antagonist RU 26752. We have no clear explanation for the variable effects of RU 26752 on mRNA and protein, but we believe that the effect observed by western blot may reflect best the aldosterone regulation of Kir4.1. Thus, on the whole, we provide data indicating that Kir4.1 may be regulated by the MR pathway (in addition to be GR dependent).

In addition, we observed a change in localization of Kir4.1 in the retina of Lewis rat eyes injected with aldosterone. In sham-injected rats, Kir4.1 is mostly located around vessels in the INL and inner plexiform layer, and in Müller end feet at the inner limiting membrane level. Intravitreous aldosterone leads to enhanced Kir4.1 immunofluorescence in the RMG apical microvilli in the OLM. These results show that aldosterone not only up-regulates Kir4.1 expression but also changes its spatial distribution within RMG cells.

Aldosterone Up-Regulates AQP4 in RMG Cells Through Specific MR Activation and in the Rat Retina In Vivo:

Müller cells are involved in retinal volume regulation, preventing excess water accumulation during neuronal activity. This is achieved by facilitated water fluxes through AQP4. When aldosterone was added to RMG primary cultures or to retinal explants, we observed an increase in AQP4 mRNA expression while the glucocorticoid agonist dexamethasone is ineffective. The aldosterone effect is fully suppressed by the MR antagonist RU26752, indicating that it depends mostly on MR activation. The GR antagonist RU38486 reduces somehow the aldosterone induction of AQP4 in rat samples, possibly due to species differences (AQP4 expression may be partially dependent on GR activated by aldosterone in the rat retina, not in human cells). Aldosterone-dependent increase in mRNA is saturated at 10 nM. The hormone also increases AQP4 expression at the protein level that is blocked by RU26752. On the whole, AQP4 appears as a bona fide mineralocorticoid-specific target in Müller cells.

We also found that aldosterone changes the pattern of expression of AQP4 within the retina. In sham-injected rats, AQP4 is located in the end feet of RMG and in RMG cell prolongations around vessels but it is not expressed at the OLM level. In aldosterone-injected eyes, AQP4 expression is not only enhanced in RMG end feet and around vessels but it also extends all along RMG prolongations up to the OLM in their apical microvilli.

Confocal imaging of flat-mounted rat retina from sham or aldosterone-injected eyes illustrates the changes in AQP4 localization induced by aldosterone in vivo. In the aldosterone-injected eyes, perivascular AQP4 fluorescence is more intense in the superficial vessels located in the GCL and NFL as well as around deep capillaries as compared to the sham-injected eyes. Moreover, there is much more AQP4 signal in the OLM in aldosterone-injected eyes as compared to the sham-injected eyes. Therefore aldosterone up-regulates the level of AQP4 expression in RMG cells and modifies its cellular distribution in vivo.

Discussion

Aldosterone and the mineralocorticoid receptor are important modulators of renal sodium reabsorption in the distal parts of the renal tubule, and also act in several non-renal tissues, including non-epithelial cells, as cardiomyocytes, vascular endothelial cells, keratinocytes or neurons. While the underlying signaling pathways remain largely undetermined, a striking feature of extra-renal effects resides in the links between excessive mineralocorticoid activation and pathology. For instance, reports on the beneficial effects of MR antagonism in cardiac failure led to the notion that excessive MR signaling produces cardio-vascular damage. In the brain, neuronal MR is likely involved in modulation of anxiety, as inferred from brain-specific over expression of the MR in mice. More recently, the eye has been also shown to express the MR and its involvement in retinal vascular pathology has been shown in a rat model of oxygen induced retinopathy. While aldosterone per se did not promote retinal angiogenesis, MR antagonism reduced the pathological angiogenesis associated with inflammation and oxidative stress in this model. This report also documented MR expression in the retina. The present study confirms that MR is expressed in ganglion cells and in cells of the inner nuclear layer. MR expression was also found in primary cultures of rat RMG and in rat retinal explants. In addition, we provide the pattern of cell-specific GR expression in the retina, which was not determined previously. We also show that the MR is co-expressed with the MR-protector enzyme HSD2, thus permitting aldosterone-specific MR occupancy and effects in RMG cells. Inactivation of the majority of glucocorticoids by HSD2, associated to post-receptor selectivity mechanisms should provide conditions for specific aldosterone actions in the retina.

As a first step to elucidate primary aldosterone effects in the healthy retina, we showed that aldosterone injection into the vitreous of the eye leads to an increase in retinal thickness 24 hrs later (reminiscent of fluid accumulation). Aldosterone also activates RMG cells as evidenced by GFAP immunostaining. Such activation indicates non specific RMG stress. To document the involvement of RMG cells, we have evaluated the effects of 24 hrs aldosterone treatment in cultured RMG cells and in retinal explants. The notion that RMG cells may be sensitive to aldosterone has been scarcely evoked previously in the literature. Of note 40 years ago it was reported that aldosterone was nearly as potent as glucocorticoids to induce glutamine synthetase activity (an enzyme specific of RMG) in the developing retina of the chick embryo.

In the kidney collecting duct, ENaC is a classical target of the aldosterone/MR. The existence of amiloride-sensitive sodium channels in RMG has been previously reported, and it has been proposed that ENaC could be involved in cell volume regulation. Our finding of enhanced ENaC-α expression in RMG after mineralo- and glucocorticoid challenges parallels several reports made on epithelial cells. It raises the question of the role of corticosteroid hormones and ENaC to adapt to cell swelling and/or to participate in fluid clearance from the retinal spaces towards retinal vessels or the vitreous. Thus aldosterone-mediated Na entry may occur in RMG cells upon hormonal challenge.

This study indicates that aldosterone up-regulates the potassium channel Kir 4.1 and the water channel AQP4. Kir4.1 is the main potassium channel of the RMG, where its polarized expression allows K influx into RMG, from the extra-cellular space surrounding activated neurons, and its delivery to the retinal blood vessels and the vitreous, a process referred as "potassium siphoning". The water channel AQP4 has been shown to allow water movement into and out of RMG cells. Evidence has been provided that water flux through AQP4 is important to control retinal swelling and cytotoxic edema. Co-expression and functional interaction of Kir4.1 with AQP4 ensure osmotic homeostasis of the inner retina. This functional interaction has been questioned recently, since Kir4.1 distribution is not affected in RMG from AQP4 knock out mice, and the reduction in water permeability in RMG from AQP4 knock out mice is not accompanied by alterations of K currents.

The data reported here have been obtained after treatment of tissue/cells with 10 nM aldosterone, i.e. a concentration that is usually found to elicit a mineralocorticoid effect ex vivo (while lower doses are indeed effective in vivo); for example, MR-mediated responses were reported to occur after challenge with at least 10 nM aldosterone in renal cells, aortic or retinal endothelial cells. To document the specificity of the observed response, we combined information issued from 1) dose-dependent aldosterone effects and competition experiments with classical MR and GR antagonists and 2) dexamethasone treatment. Altogether (and despite some difference in response depending on the species/tissue/cell context and certain degree of overlapping between aldosterone and glucocorticoid control of gene expression in retinal cells), it appears that ENaC and Kir 4.1 may be under the coordinate control of GR/MR, while AQP4 is essentially regulated by MR activation by aldosterone. It is generally considered that MR and GR exert partially overlapping control of gene expression, although with variations in the relative contribution of each receptor, according to the cell context. However, MR and GR are not redundant, as the inactivation of each receptor leads to perinatal mortality that cannot be rescued by the other receptor.

We found that 24 hrs aldosterone treatment also promotes the localization of Kir4.1 and AQP4 towards the apical region of RMG in the outer retina facing the retinal pigment epithelium (RPE) that forms the barrier between neuroretina and choroidal vessels. This indicates that enhanced mineralocorticoid signaling in healthy retina may modify normal fluid homeostasis within the different compartments of the retina. The enhanced thickness of the retina observed after intravitreous aldosterone injection suggests fluid accumulation. Relocalization of channels in the region of the Müller cells facing the RPE and choroidal capillaries should favor fluid movement from the Müller cells towards the subretinal space. However, retinal fluid clearance through the RPE towards choroidal capillaries may be insufficient to overcome aldosterone-driven AQP4/Kir4.1-mediated fluid movements in the outermost part of the retina, leading to retinal swelling. An increased AQP4 expression has been reported in the hypoxic retina, that present with swelling of astrocytes and Müller cells. Thus, our results are in accordance with the notion that AQP4 plays an important role in retinal swelling.

In diabetes, excessive MR activity has been inferred from the efficiency of MR antagonism to limit tissue injury, as documented in renal tissue. Whether impaired aldosterone/MR signaling may be involved in the constitution of chronic retinal edema, as in diabetic retinopathy, remains to be investigated. This is obviously a crucial issue, as MR activity may be blocked by intravitreous injections of antagonists as spironolactone or eplerenone.

In conclusion, this report identifies a new signaling pathway by which the hormone aldosterone contributes to retinal fluid homeostasis. It should provide rationale for further investigation of retinal MR function in pathology, in particular in diabetes.

EXAMPLE 2

Co-Administration of Small Amounts of Glucocorticoids with MR Antagonists is Particularly Suitable for the Treatment of Fluid Accumulation in and/or Under the Retina Associated with Diabetic Retinopathy, Glaucoma, Ischemia, Myopia, Central Serous Chorioretinitis, or the Exudative Forms of Age Related Macular Degeneration We have performed several experiments. The results of which show the following:
- aldosterone up-regulates the mRNA expression of the water channel AQP4 in RMG cells; co-administration of aldosterone and a MR specific antagonist (RU26752) completely blocks the induction, showing that AQP4 up-regulation occurs via MR occupancy.
- triamcinolone (TA) reduces the expression of AQP4, an effect clearly opposed to that of aldosterone, thus mimicking the effect of the MR specific antagonist does. Therefore, glucocorticoids and MR antagonists have comparable effect on AQP4 expression, suggesting that administration of MR antagonists will provide antiedematous effects in retina comparable to those observed during triamcinolone treatment.
- glucocorticoid dexamethasone (Dex) decreases the MR gene expression, an effect not reversed by the addition of MR antagonists.

Therefore the administration of small amounts of glucocorticoids with MR antagonists will be particularly suitable for the treatment of fluid accumulation in and/or under the retina associated with diabetic retinopathy, glaucoma, ischemia, myopia, central serous chorioretinitis, or the exudative forms of age related macular degeneration. Indeed such combination will avoid the deleterious effects induced by MR activation in the retina.

EXAMPLE 3

Central Serous Chorioretinopathy

Central serous chorioretinopathy (CSCR) is an acute serous retinal detachment, affecting mostly the posterior pole and more specifically the macula. The disease begins with dilation of choroidal vessels, then opening of junctions in retinal pigment epithelial cells (RPE) and then fluid accumulation under and/or in the retina.

Among recognized risk factors, corticotherapy and stress are identified as major events. The mechanism by which steroids induce this fluid accumulation under the macula is not known.

The condition resolves spontaneously in about three months in 70% of the cases but chronicity can be observed and results in poor visual acuity. In about 40% of the cases, recurrences can be observed leading to diffuse retinal epitheliopathy. In chronic conditions macular intra retinal fluid accumulation, eventually forming cysts can be observed.

We have hypothesized that CSCR could be efficiently treated with MR antagonists due to the fact that inappropriate MR activation in the retina by endogenous cortisol or corticotherapy could interfere with endogenous-fluid-drainage mechanisms.

Figure 2:
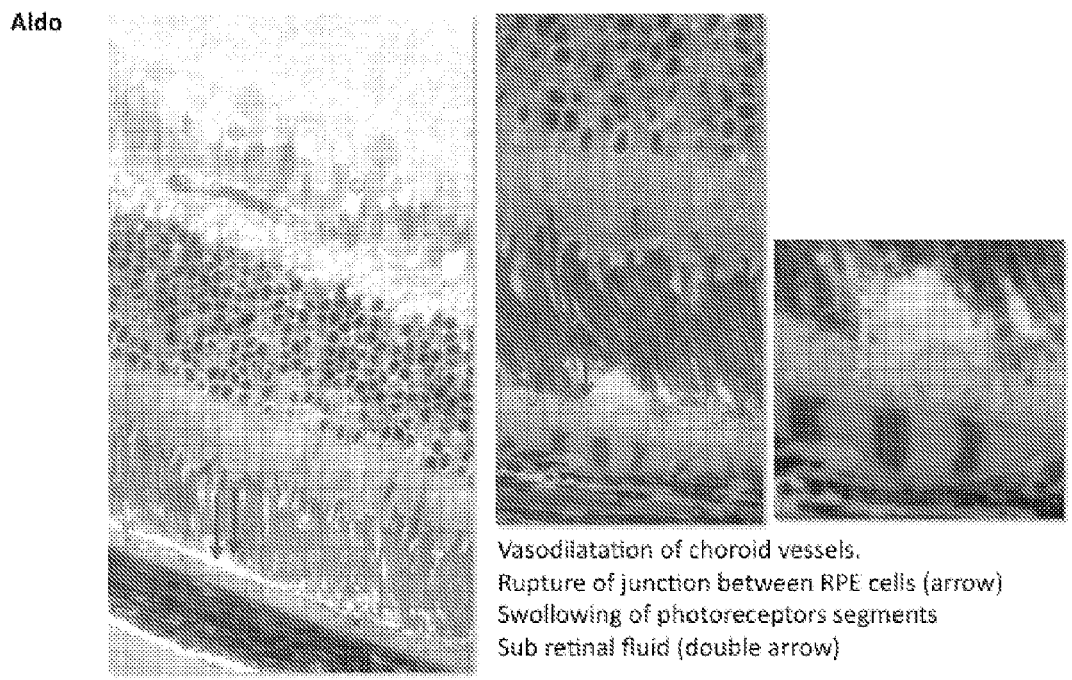
FIG. 2 depicts vasodilation of choroid vessels, rupture of the junction between RPE cells, swallowing of the photoreceptor segments and sub retinal fluid accumulation in the Brown Norway rat models following aldosterone injection.

We demonstrate here that Brown Norway rats that carries a gain of function mutation in the MR gene, and receiving an intraocular injection of aldosterone or corticosterone, the endogenous corticosteroid of the rat, develop a retinal pathology very close to CSCR (FIGS. 1 and 2).

Patients with non-resolutive or chronic diffuse epitheliopathy presenting with macular fluid accumulation have been treated with oral eplerenone, a specific MR antagonist.

Figure 3:
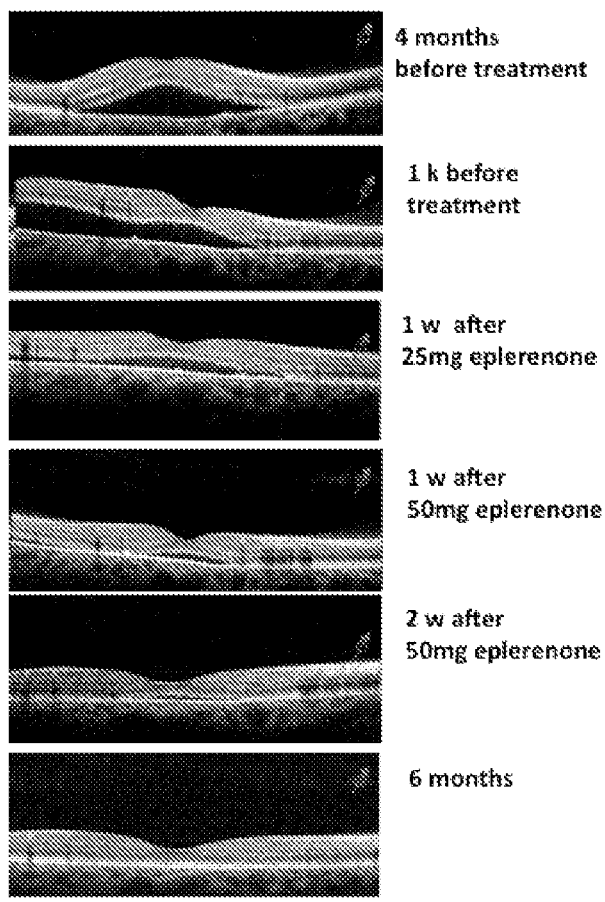
FIG. 3 depicts a patient presenting with CSCR and followed for 4 months without resolution of the sub retinal fluid accumulation in the retina. After 4 months and at 1 week before treatment, the amount of fluid had accumulated. The patient received 25 mg/day orally of eplerenone, a specific mineraloreceptor antagonist, for 8 days, and showed a striking reduction in the sub retinal fluid. The dose of eplerenone was augmented to 50 mg/day for 8 days, resulting in improvement with almost complete resolution after 2 weeks of treatment. The treatment was discontinued after 4 weeks of treatment and at 6 months the patient did not show any recurrence.
Figure 4:
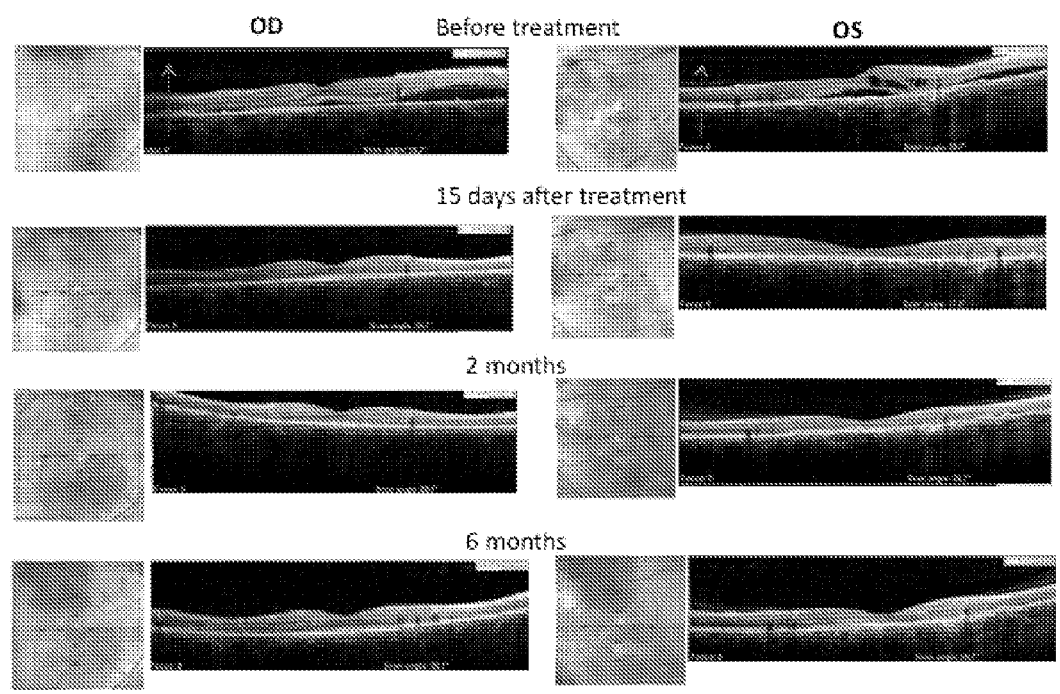
FIG. 4 depicts a patient with a chronic form of CSCR (or diffuse epitheliopathy) and having a long history of recurrent CSCR on both eyes. The left eye (OS) presents a macular edema with sub retinal fluid and retinal cysts. Improvement is observed in the left eye following treatment.

FIGS. 3 and 4 show examples of patients treated by eplerenone. As shown, eplerenone induces a very rapid and efficient regression of sub retinal and/or intra retinal fluid in the retina. The kinetics of efficacy is as early as the first week of use.

FIG. 3 shows the case of a patient presenting with CSCR and followed for 4 months without resolution of the sub retinal fluid accumulation in the retina. On the contrary, 4 months later and at 1 week before treatment, the amount of fluid had accumulated. The patient received 25 mg/day orally of eplerenone, a specific mineraloreceptor antagonist, for 8 days, and showed a striking reduction in the sub retinal fluid. Then the dose of eplerenone was augmented to 50 mg/day for 8 days and he showed again improvement with almost complete resolution after 2 weeks of treatment. The treatment was discontinued after 4 weeks of treatment and at 6 months the patient did not show any recurrence.

FIG. 4 shows the case of a patient with a chronic form of CSCR (or diffuse epitheliopathy). He has a long history of recurrent CSCR on both eyes. In his left eye (OS), he presents a macular edema with sub retinal fluid and retinal cysts. The left eye vision is reduced to 1/10 and the edema is chronic since more than 2 years.

His right eye (OD) is the only functional eye and presents also since a few weeks a sub retinal fluid accumulation.

He has been treated with eplerenone 25 mg/day for 8 days and then 50 mg/days for 3 month. As early as 15 days after treatment, there is a complete resolution of the sub retinal fluid in both eyes and surprisingly also total resolution of the macular cysts that were chronic since months. Moreover, vision in the left eye recovered to 6/10. No recurrence was observed on none of the eyes even at 6 months.

Conclusions

Taken together, our experimental results together with the clinical effects of MR antagonists demonstrate that MR activation induces sub retinal fluid accumulation and that MR antagonists are efficient to treat patients presenting with sub retinal and/or intra retinal fluid accumulation due to CSRC or diffuse epiteliopathy.

EXAMPLE 4

Additional Results on Diabetic Retinopathy

Goto-Kakizaki (GK) rats have been used as model for diabetic retinopathy.

The animals used in this work were treated in accordance with the Association for Research in Vision and Ophthalmology (ARVO). Experimental procedures were submitted and approved by the ethic committee of Paris Descartes University GK rats (Taconic Europe, Denmark), a Wistar non-obese model of Non-Insulin Dependent type 2 Diabetes were used at different ages of hyperglycemia. Glycemia was measured using Accutrend GC and Accu-check compact equipments (Roche) and plasma glucose >250 mg/dl was considered as diabetic state. GK diabetic rats had hyperglycemia from 14 weeks after birth to the time of sacrifice, as compared to controls. Controls were selected from age-matched non-diabetic rats and with plasma glucose <150 mg/dl.

Figure 5:
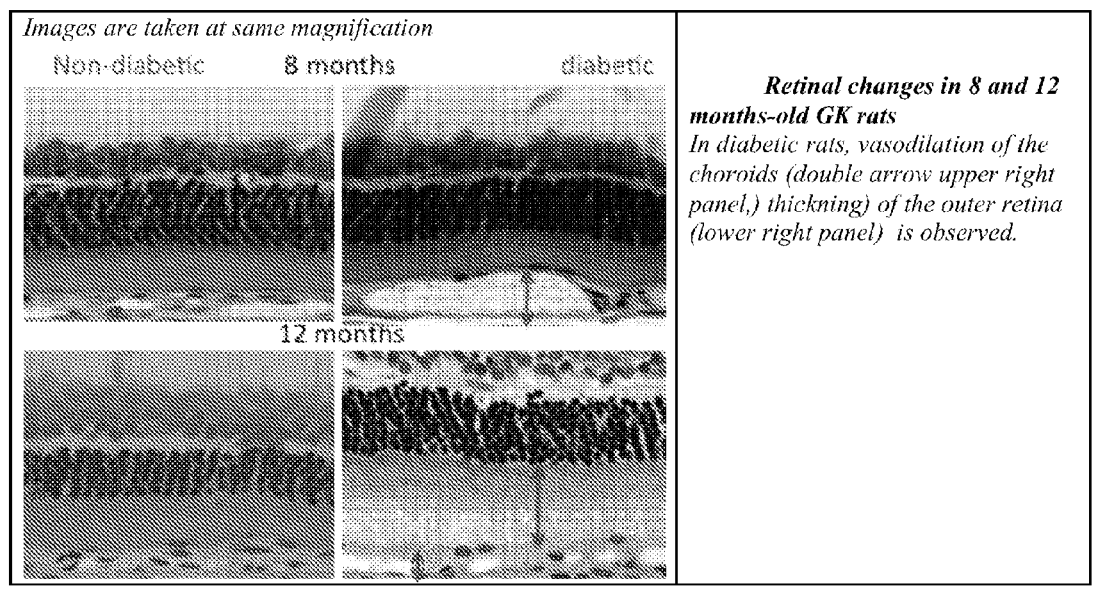
FIG. 5 depicts retina pathology occurring in GK rats at 8 and 12 months

FIG. 5 shows the retina pathology occurring in GK rats at 8 and 12 months.

Figure 6:
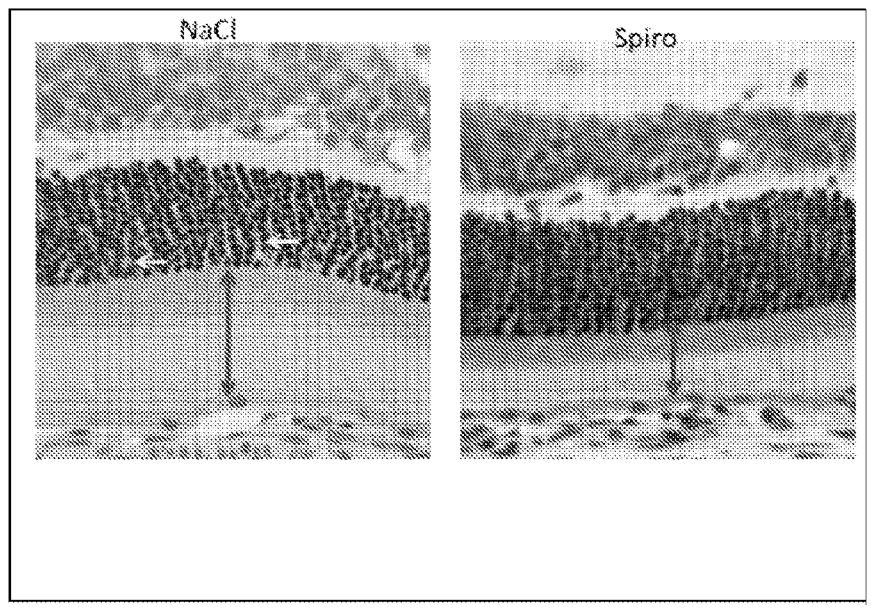
FIG. 6 depicts the effect of intra vitreal injection of spironolactone (1 µM in the vitreous) in GK rats.

FIG. 6 shows the effect of intravitreal injection of sprironolactone (1 μM final in the vitreous) in GK rats.

24 hrs after injection (right panel), the thickness of the outer retina is decreased (red double arrow) and fluid accumulation in the outer nuclear layer (photoreceptor layer) (yellow arrow) have decreased.

In 18 months-old GK rats, electroretinogramms were preformed (ERG). In those animals, the a- and b-wave are significantly reduced as compared to ERG performed at 3 months, at the onset of diabetes.

18 months diabetic rats were treated with intravitreous injections (1 μM) at day 1,3,5 and animals were re tested for ERGs 24 hrs after each injection.

24 hrs after the third injection, animals were sacrificed and the retina were analyzed using semi-thin sections.

Figure 7:
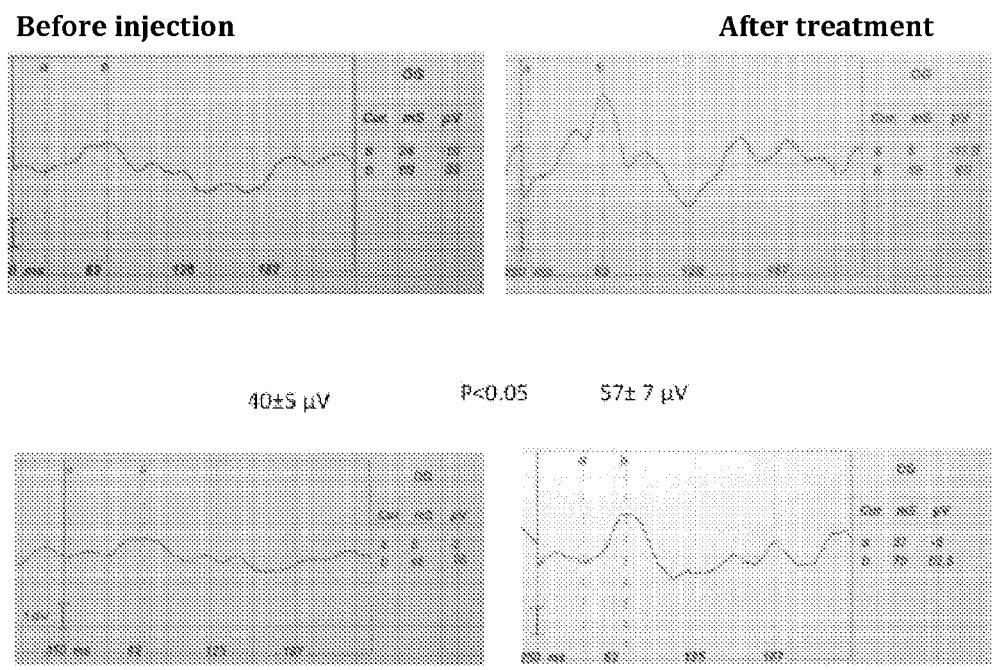
FIG. 7 depicts the ERGs in GK rats taken before treatment and 24 hrs after the last spironolactone injection.

FIG. 7 shows the ERGs performed before treatment and 24 hrs after the last spironolactone injection.

As shown on this example, the b-wave is significantly increased after treatment as compared to before treatment (left panel) and after treatment (right panel).

After sacrifice, eyes were sectioned.

Figure 8:
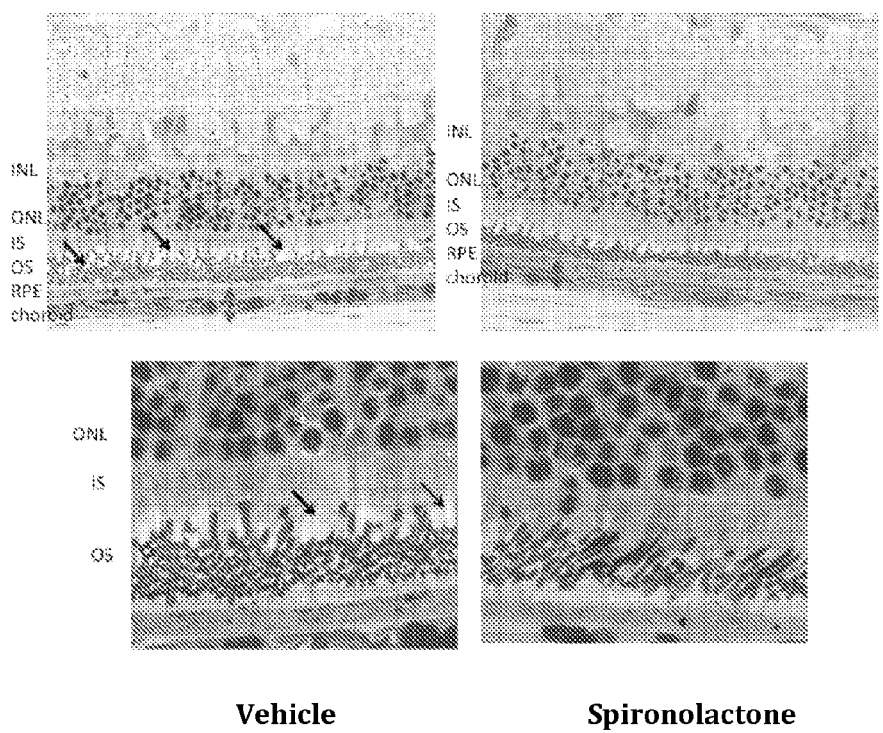
FIG. 8 depicts GK rats that have been treated with the vehicle present edema in the outer retina, edema in the outer nuclear layer, and dilated choriocapillaries (arrows) relative to spironolactone treated GK rates.

FIG. 8 shows that GK rats that have been treated with the vehicle present edema in the outer retina (black arrows, left panel>> and edema in the outer nuclear layer (yellow arrow). The choriocapillaries is dilated (double red arrow).

In the treated eye, there edema has decreased I both the inner/outer (IS/OS) segments and in the outer nuclear layer (ONL). Vasodilation has reduced in the choriocapillaries.

Conclusions

Intraocular spironolactone efficiently reduces retinal edema in GK diabetic rats and improves the formation of outer segments. These changes are correlated with improved function of the retina as demonstrated by ERGs.

This demonstrates the beneficial effect of intraocular sprironolactone in diabetic retinal fluid accumulation.

REFERENCES

Throughout this application, various references describe the state of the art to which this invention pertains. The disclosures of these references are hereby incorporated by reference into the present disclosure.

The invention claimed is:

1. A method for the treatment of fluid accumulation in and/or under the retina in a subject who has diabetic retinopathy, the method comprising administering a biodegradable ocular implant comprising a mineralocorticoid receptor (MR) antagonist to the eye of the subject.

2. The method according to claim 1, wherein the mineralocorticoid receptor (MR) antagonist is a spirolactone-type steroidal compound.

3. The method according to claim 2, wherein the mineralocorticoid receptor (MR) antagonist is eplerenone.

* * * * *